(12) United States Patent
Imanishi et al.

(10) Patent No.: US 7,427,672 B2
(45) Date of Patent: Sep. 23, 2008

(54) ARTIFICIAL NUCLEIC ACIDS OF N-O BOND CROSSLINKAGE TYPE

(75) Inventors: Takeshi Imanishi, 2-18, Chiyogaoka 2-chome, Nara-shi, Nara 631-0045 (JP); Satoshi Obika, Takatsuki (JP); Kazuyuki Miyashita, Minno (JP)

(73) Assignee: Takeshi Imanishi, Nara (JP)

( * ) Notice: Subject to any disclaimer, the term of this patent is extended or adjusted under 35 U.S.C. 154(b) by 0 days.

(21) Appl. No.: 10/569,949

(22) PCT Filed: Aug. 25, 2004

(86) PCT No.: PCT/JP2004/012173

§ 371 (c)(1),
(2), (4) Date: Jan. 8, 2007

(87) PCT Pub. No.: WO2005/021570

PCT Pub. Date: Mar. 10, 2005

(65) Prior Publication Data

US 2007/0167387 A1    Jul. 19, 2007

(30) Foreign Application Priority Data

Aug. 28, 2003    (JP) .............................. 2003-304847

(51) Int. Cl.
*C07H 19/00*    (2006.01)
*C07H 21/00*    (2006.01)
*A01N 43/04*    (2006.01)
*A61K 31/70*    (2006.01)

(52) U.S. Cl. ......................... 536/22.1; 536/23.1; 514/43

(58) Field of Classification Search ........................ None
See application file for complete search history.

(56) References Cited

U.S. PATENT DOCUMENTS

| 6,670,461 B1 | 12/2003 | Wengel et al. |
| 6,794,499 B2 | 9/2004 | Wengel et al. |
| 2002/0068708 A1 | 6/2002 | Wengel et al. |
| 2003/0028013 A1 | 2/2003 | Wang et al. |
| 2003/0134808 A1 | 7/2003 | Wengel |
| 2003/0144231 A1 | 7/2003 | Wengel et al. |

FOREIGN PATENT DOCUMENTS

| JP | 2002-516256 A | 6/2002 |
| JP | 2002-521310 A | 7/2002 |
| WO | WO-03/068795 A1 | 8/2003 |

OTHER PUBLICATIONS

Hair et al. Nucleic Acids Research Supplement No. 2 (2002), pp. 147-148.*
Obika et al. Tetrahedron Letters (2000), vol. 41, pp. 8923-8927.*
Obika et al. Nucleic Acids Research Supplement No. 1 (2001), pp. 145-146.*
Obika et al. Nucleic Acids Research Supplement No. 2 (2002), pp. 25-26.*
Burgers et al., "Diastereomers of 5'-O-Adensoyl 3'-O-Uridyl Phosphorothioate: Chemical Synthesis and Enzymatic Properties," BIOCHEMISTRY, vol. 18, No. 4, pp. 592-596 (1979).
Miller et al., "Use of methylphosphonic dichloride for the synthesis of oligonucleoside methylphosphoriates," Nucleic Acids Research, vol. 11 No. 15, pp. 5189-5204 (1983).
Vandendriessche et al., "Synthesis, Enzymatic Stability and Base-paring Properties of Oligothymidylates Containing Thymidine Dimers with Different N-Substituted Guanidine Linkages," J. Chem. Soc Perkin Trans. vol. 1, pp. 1567-1575 (1993).
Nielsen et al., "Sequence-Selective Recognition of DNA by Strand Displacement with a Thymine-Substituted Polyamide." SCIENCE, vol. 254, pp. 1497-1500 (1991).
Applied Antisense Oligonucleotide Technology, Willy-Liss, pp. 1-6 (1998).
Moldave, Progess in Nucleic Acid Research and Molecular Biology, vol. 69, pp. 1-47 (2001), Academic Press.
S. Elbashir et al., "Duplexes of 21 - nucleotide RNAs mediate RNA interference in cultured mammallan cells," Nature, vol. 411, pp. 494-498 (2001).

* cited by examiner

*Primary Examiner*—Patrick T Lewis
(74) *Attorney, Agent, or Firm*—Birch, Stewart, Kolasch & Birch, LLP

(57) ABSTRACT

An oligonucleotide analogue useful for the antisense method, etc., having excellent enzyme resistance, having potent selective binding affinity for single-stranded RNA, and further having an excellent triplex-forming capacity with double-stranded DNA, and a nucleoside analogue useful for its production are provided.

Nucleoside analogues, which are compounds of the general formula (I) and salts thereof, and oligonucleotide analogues containing one or more of the nucleoside analogues:

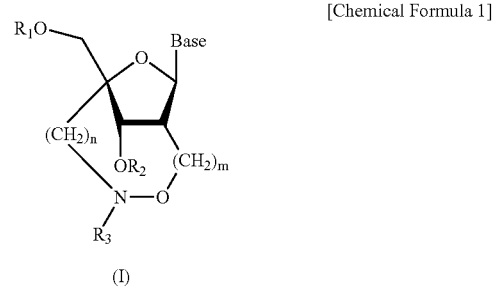

[Chemical Formula 1]

(I)

where Base is an aromatic heterocyclic group or the like optionally having a substituent; $R_1$, $R_2$ and $R_3$ are each a hydrogen atom, a protective group for an amino group, a protective group for a hydroxyl group, a phosphate group, or —P($R_4$)$R_5$ [where $R_4$ and $R_5$ are each a hydroxyl group, a protected hydroxyl group, a mercapto group, a protected mercapto group, etc.]; m=0 to 2; and n=1 to 3].

20 Claims, 1 Drawing Sheet

Evaluation of Enzyme Resistance
(2',4'-BNA$^{NC}$ oligonucleotide, SVPDE 0.5 μg/ml)

SEQUENCE LISTING

<160> NUMBER OF SEQ ID NOS: 34

<210> SEQ ID NO 1
<211> LENGTH: 12

-continued

```
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(6)
<223> OTHER INFORMATION: n is a, c, g, t, unknown, or other

<400> SEQUENCE: 1
gcgttntttg ct                                                         12

<210> SEQ ID NO 2
<211> LENGTH: 12
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other

<400> SEQUENCE: 2
gcgttntntg ct                                                         12

<210> SEQ ID NO 3
<211> LENGTH: 12
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (4)..(4)
<223> OTHER INFORMATION: n is a, c, g, t, unknown, or other
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other

<400> SEQUENCE: 3
gcgntntntg ct                                                         12

<210> SEQ ID NO 4
<211> LENGTH: 12
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(8)
<223> OTHER INFORMATION: n is a, c, g, t, unknown, or other

<400> SEQUENCE: 4
gcgttnnntg ct                                                         12

<210> SEQ ID NO 5
<211> LENGTH: 12
<212> TYPE: DNA
<213> ORGANISM: Artificial Sequence
<220> FEATURE:
```

```
<223> OTHER INFORMATION: Chemically Synthesized Antisense Strand
<220> FEATURE:
<221> NAME/KEY: misc_feature
<222> LOCATION: (4)..(9)
<223> OTHER INFORMATION: n is a, c, g, t, unknown, or other

<400> SEQUENCE: 5
gcgnnnnnng ct                                                              12

<210> SEQ ID NO 6
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other
<220> FEATURE:
<221> NAME/KEY: misc_feature
<222> LOCATION: (10)..(10)
<223> OTHER INFORMATION: n is a, c, g, t, unknown, or other
<220> FEATURE:
<221> NAME/KEY: misc_feature
<222> LOCATION: (12)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 6
tttttntntn tntnt                                                           15

<210> SEQ ID NO 7
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (5)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other
<220> FEATURE:
<221> NAME/KEY: misc_feature
<222> LOCATION: (10)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 7
ttttnntntn nntnt                                                           15

<210> SEQ ID NO 8
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
```

```
<222> LOCATION: (6)..(10)
<223> OTHER INFORMATION: n is a, c, g, t, unknown, or other
<220> FEATURE:
<221> NAME/KEY: misc_feature
<222> LOCATION: (12)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 8
tttttnnnnn tntnt                                                    15

<210> SEQ ID NO 9
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (1)..(1)
<223> OTHER INFORMATION: n is a, c, g, t, unknown, or other
<220> FEATURE:
<221> NAME/KEY: misc_feature
<222> LOCATION: (3)..(3)
<223> OTHER INFORMATION: n is a, c, g, t, unknown, or other
<220> FEATURE:
<221> NAME/KEY: misc_feature
<222> LOCATION: (5)..(7)
<223> OTHER INFORMATION: n is a, c, g, t, unknown, or other
<220> FEATURE:
<221> NAME/KEY: misc_feature
<222> LOCATION: (9)..(14)
<223> OTHER INFORMATION: n is a, c, g, t, unknown, or other

<400> SEQUENCE: 9
ntntnnntnn nnnnt                                                    15

<210> SEQ ID NO 10
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (2)..(2)
<223> OTHER INFORMATION: n is a, c, g, t, unknown, or other
<220> FEATURE:
<221> NAME/KEY: misc_feature
<222> LOCATION: (5)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other
<220> FEATURE:
<221> NAME/KEY: misc_feature
<222> LOCATION: (10)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 10
tnttnntntn nntnt                                                    15

<210> SEQ ID NO 11
<211> LENGTH: 15
<212> TYPE: DNA
```

```
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (1)..(1)
<223> OTHER INFORMATION: n is a, c, g, t, unknown, or other
<220> FEATURE:
<221> NAME/KEY: misc_feature
<222> LOCATION: (5)..(6)
<223> OTHER INFORMATION: n is a, c, g, t, unknown, or other
<220> FEATURE:
<221> NAME/KEY: misc_feature
<222> LOCATION: (9)..(10)
<223> OTHER INFORMATION: n is a, c, g, t, unknown, or other
<220> FEATURE:
<221> NAME/KEY: misc_feature
<222> LOCATION: (12)..(14)
<223> OTHER INFORMATION: n is a, c, g, t, unknown, or other

<400> SEQUENCE: 11
ntttnnttnn tnnnt                                                      15

<210> SEQ ID NO 12
<211> LENGTH: 10
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (9)..(9)
<223> OTHER INFORMATION: n is a, c, g, t, unknown, or other

<400> SEQUENCE: 12 tttttttnt                                                             10

<210> SEQ ID NO 13
<211> LENGTH: 12
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(6)
<223> OTHER INFORMATION: n is a, c, g, t, unknown, or other

<400> SEQUENCE: 13
gcgttntttg ct                                                         12

<210> SEQ ID NO 14
<211> LENGTH: 12
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other

<400> SEQUENCE: 14
gcgttntntg ct                                                         12

<210> SEQ ID NO 15
<211> LENGTH: 12
```

```
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (4)..(4)
<223> OTHER INFORMATION: n is a, c, g, t, unknown, or other
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other

<400> SEQUENCE: 15
gcgntntntg ct                                                          12

<210> SEQ ID NO 16
<211> LENGTH: 12
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(8)
<223> OTHER INFORMATION: n is a, c, g, t, unknown, or other

<400> SEQUENCE: 16
gcgttnnntg ct                                                          12

<210> SEQ ID NO 17
<211> LENGTH: 12
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (4)..(9)
<223> OTHER INFORMATION: n is a, c, g, t, unknown, or other

<400> SEQUENCE: 17
gcgnnnnnng ct                                                          12

<210> SEQ ID NO 18
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other
<220> FEATURE:
<221> NAME/KEY: misc_feature
<222> LOCATION: (10)..(10)
<223> OTHER INFORMATION: n is a, c, g, t, unknown, or other
<220> FEATURE:
<221> NAME/KEY: misc_feature
<222> LOCATION: (12)..(12)
<223> OTHER INFORMATION: n is a, c, g, t, unknown, or other
<220> FEATURE:
<221> NAME/KEY: misc_feature
<222> LOCATION: (14)..(14)
```

-continued

<223> OTHER INFORMATION: n is a, c, g, t, unknown, or other

<400> SEQUENCE: 18
tttttntntn tntnt                                                                                                 15

<210> SEQ ID NO 19
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (5)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other
<220> FEATURE:
<221> NAME/KEY: misc_feature
<222> LOCATION: (10)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 19
ttttnntntn nntnt                                                                                                 15

<210> SEQ ID NO 20
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (6)..(10)
<223> OTHER INFORMATION: n is a, c, g, t, unknown, or other
<220> FEATURE:
<221> NAME/KEY: misc_feature
<222> LOCATION: (12)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 20
tttttnnnnn tntnt                                                                                                 15

<210> SEQ ID NO 21
<211> LENGTH: 15
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (1)..(1)
<223> OTHER INFORMATION: n is a, c, g, t, unknown, or other
<220> FEATURE:
<221> NAME/KEY: misc_feature
<222> LOCATION: (3)..(3)
<223> OTHER INFORMATION: n is a, c, g, t, unknown, or other
<220> FEATURE:
<221> NAME/KEY: misc_feature
<222> LOCATION: (5)..(7)
<223> OTHER INFORMATION: n is a, c, g, t, unknown, or other
<220> FEATURE:
<221> NAME/KEY: misc_feature

```
<222> LOCATION: (9)..(14)
<223> OTHER INFORMATION: n is a, c, g, t, unknown, or other

<400> SEQUENCE: 21
ntntnnntnn nnnnt                                                      15

<210> SEQ ID NO 22
<211> LENGTH: 10
<212> TYPE: DNA
<213> ORGANISM: Artificial Sequence
<220> FEATURE:
<223> OTHER INFORMATION: Chemically Synthesized Antisense Strand
<220> FEATURE:
<221> NAME/KEY: misc_feature
<222> LOCATION: (9)..(9)
<223> OTHER INFORMATION: n is a, c, g, t, unknown, or other

<400> SEQUENCE: 22 tttttttnt                                                             10

<210> SEQ ID NO 23
<211> LENGTH: 12
<212> TYPE: DNA
<213> ORGANISM: Artificial Sequence
<220> FEATURE:
<223> OTHER INFORMATION: Chemically Synthesized

<400> SEQUENCE: 23
agcaaaaaac gc                                                         12

<210> SEQ ID NO 24
<211> LENGTH: 12
<212> TYPE: DNA
<213> ORGANISM: Artificial Sequence
<220> FEATURE:
<223> OTHER INFORMATION: Chemically Synthesized Antisense Strand

<400> SEQUENCE: 24
gcgttttttg ct                                                         12

<210> SEQ ID NO 25
<211> LENGTH: 12
<212> TYPE: RNA
<213> ORGANISM: Artificial Sequence
<220> FEATURE:
<223> OTHER INFORMATION: Chemically Synthesized

<400> SEQUENCE: 25
agcaaaaaac gc                                                         12

<210> SEQ ID NO 26
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 26
gctaaaaaga aagagagatc g                                               21

<210> SEQ ID NO 27
<211> LENGTH: 21
<212> TYPE: DNA
<213> ORGANISM: Artificial Sequence
<220> FEATURE:
<223> OTHER INFORMATION: Chemically Synthesized
```

```
<400> SEQUENCE: 27
cgatctctct ttcttttag c                                       21

<210> SEQ ID NO 28
<211> LENGTH: 15
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (10)..(10)
<223> OTHER INFORMATION: n is a, c, g, t, unknown, or other
<220> FEATURE:
<221> NAME/KEY: misc_feature
<222> LOCATION: (12)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 28
tttttntttn tntnt                                              15

<210> SEQ ID NO 29
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 29
gctgctaaaa agaaagagag atcgtcg                                 27

<210> SEQ ID NO 30
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 30
cgacgatctc tctttctttt tagcagc                                 27

<210> SEQ ID NO 31
<211> LENGTH: 15
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (6)..(6)
<223> OTHER INFORMATION: n is a, c, g, t, unknown, or other
<220> FEATURE:
<221> NAME/KEY: misc_feature
<222> LOCATION: (8)..(8)
<223> OTHER INFORMATION: n is a, c, g, t, unknown, or other
<220> FEATURE:
```

```
<221> NAME/KEY: misc_feature
<222> LOCATION: (10)..(10)
<223> OTHER INFORMATION: n is a, c, g, t, unknown, or other
<220> FEATURE:
<221> NAME/KEY: misc_feature
<222> LOCATION: (12)..(12)
<223> OTHER INFORMATION: n is a, c, g, t, unknown, or other
<220> FEATURE:
<221> NAME/KEY: misc_feature
<222> LOCATION: (14)..(14)
<223> OTHER INFORMATION: n is a, c, g, t, unknown, or other

<400> SEQUENCE: 31
tttttntntn tntnt                                              15

<210> SEQ ID NO 32
<211> LENGTH: 21
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (11)..(11)
<223> OTHER INFORMATION: n is a, c, g, t, unknown, or other

<400> SEQUENCE: 32
gctaaaaaga nagagagatc g                                       21

<210> SEQ ID NO 33
<211> LENGTH: 21
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (11)..(11)
<223> OTHER INFORMATION: n is a, c, g, t, unknown, or other

<400> SEQUENCE: 33
cgatctctct ntcttttag c                                        21

<210> SEQ ID NO 34
<211> LENGTH: 10
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (9)..(9)
<223> OTHER INFORMATION: n is a, c, g, t, unknown, or other

<400> SEQUENCE: 34 tttttttnt                                                     10
```

ARTIFICIAL NUCLEIC ACIDS OF N-O BOND CROSSLINKAGE TYPE

TECHNICAL FIELD

This invention relates to oligonucleotide analogues, which have stable and excellent antisense or antigene activity or have excellent activities as reagents for detection of particular genes, or as primers for initiation of amplification, or which are useful as materials for various physiological and bioactive substances and pharmaceuticals, functional materials for double-stranded oligonucleotides for RNA interference method (RNAi or siRNA) or decoy method, functional materials for DNA chips or molecular beacons targeting single-stranded nucleic acids such as cDNA, functional materials for applications to various antisense methods (including ribozymes and DNAzymes), antigene method, and genetic homologous recombination, and materials for high sensitivity analysis of biological trace components by combinations with fluorescent or luminescent substances. The invention also relates to nucleoside analogues which are intermediates for production of the oligonucleotide analogues.

BACKGROUND ART

In 1978, it was reported for the first time that an antisense oligonucleotide (antisense molecule) inhibited infection by influenza virus. Reports followed that antisense oligonucleotides also inhibited oncogene expression and AIDS infection. Since antisense oligonucleotides specifically control the expression of untoward genes, they are one of the fields that have been expected most in recent years.

The antisense method is based on the concept that the flow of information in the so-called central dogma, i.e., DNA→mRNA→protein, is to be controlled using an antisense oligonucleotide.

However, if a natural DNA or RNA oligonucleotide was applied as an antisense molecule to this method, the problem arose that it was hydrolyzed by an in vivo enzyme, or its cell membrane permeation was not high. To resolve such problems, numerous nucleic acid derivative were synthesized, and extensively studied. For example, phosphorothioates having an oxygen atom on the phosphorus atom substituted by a sulfur atom, and methyl phosphonates having a methyl group as a substituent were synthesized. Recently, products having the phosphorus atom also substituted by a carbon atom, or molecules having a ribose converted into an acyclic skeleton form have been synthesized (F. Eckstein et al., Biochem., 18, 592(1979); P. S. Miller et al., Nucleic Acids Res., 11, 5189 (1983); P. Herdewijn et al., J. Chem. Soc. Perkin Trans. 1, 1567(1993); P. E. Nielsen et al., Science, 254, 1497(1991)); C. A. Stein and A. M. Krieg (ed) "Applied Antisense Oligonucleotide Technology," Willy-Liss (1998); and J. J. Toulme et al., Prog. Nucl. Acid Rev. Mol. Biol., 67, 1(2001)).

However, none of the artificial oligonucleotides have obtained nucleoside and oligonucleotide analogues fully satisfactory in terms of a duplex-forming capacity with single-stranded RNA and DNA, a triplex-forming capacity with double-stranded DNA, in vivo stability, or ease of synthesis of oligonucleotides.

DISCLOSURE OF THE INVENTION

Problems to be Solved by the Invention

In the light of the above-described conventional technologies, it is desired to provide a nucleotide analogue which highly penetrates the cell membrane in vivo, which minimally undergoes hydrolysis by enzymes, which is easy to synthesize, and which is useful for the antisense method, the antigene method, the RNA interference method, the genetic homologous recombination method, and the decoy method.

Means for Solving the Problems

The inventors of the present invention designed a nucleic acid analogue having the sugar portion of a nucleic acid modified (i.e., artificial nucleic acid) which may be useful as a material for various physiological and bioactive substances and pharmaceuticals, a functional material for double-stranded oligonucleotides for the RNA interference method (Nature, Vol. 411, 494-498, 2001) or the decoy method, a functional material for DNA chips or molecular beacons targeting single-stranded nucleic acids such as cDNA, a functional material for applications to various antisense methods (including ribozymes and DNAzymes), the antigene method, and the genetic homologous recombination method, and a material for high sensitivity analysis of biological trace components by combinations with fluorescent or luminescent substances. The inventors synthesized the nucleic acid analogue and confirmed its usefulness.

As will be described in detail by Examples and Experimental Examples to be offered later, a DNA or RNA oligonucleotide analogue (II) containing an artificial nucleic acid 2',4'-BNA$^{NC}$ unit [in the general formula (I), $R_1$ and $R_2$ are each hydrogen, and $R_3$ is hydrogen or a methyl group], which is one aspect of the present invention, was confirmed to have the following excellent characteristics:

(1) Has a very high duplex-forming capacity with a complementary RNA strand.

Whenever one 2',4'-BNA$^{NC}$ unit is introduced into a DNA oligonucleotide (per modification), the Tm value rises by 3 to 6° C. Nevertheless, there is little increase (improvement) in the duplex-forming capacity with a complementary DNA strand. In connection with this characteristic, a dramatic increase in the Tm value (marked improvement in the duplex-forming capacity) is present in binding affinity for a complementary RNA strand, as in the case of a 2',4'-BNA-modified DNA oligonucleotide. On the other hand, the 2',4'-BNA-modified DNA oligonucleotide shows an improvement in the duplex-forming capacity with a complementary DNA strand (has the Tm value increased by 2 to 4° C. per modification), as compared with an unmodified DNA oligonucleotide. By contrast, the above-mentioned 2',4'-BNA$^{NC}$-modified DNA oligonucleotide shows little improvement in binding affinity for a DNA strand. Thus, this 2',4'-BNA$^{NC}$-modified DNA oligonucleotide is very superior in selective binding affinity for a RNA strand.

(2) The 2',4'-BNA$^{NC}$-modified DNA oligonucleotide also excels in a triplex-forming capacity with a double-stranded DNA chain.

When one 2',4'-BNA$^{NC}$ unit is introduced into a DNA oligonucleotide, the Tm value rises by 7 to 12° C. in forming a triplex with a double-stranded DNA chain. Triplex formation requires sequence selectivity such that base sequences should be strictly distinguished, and binding only to a target sequence should be effected. The difference in the Tm value of the 2',4'-BNA$^{NC}$-modified DNA oligonucleotide with respect to a match sequence and a mismatch sequence is 25°

C. or higher. Thus, this oligonucleotide has excellent sequence selectivity surpassing that of a natural DNA oligonucleotide.

(3) Nuclease resistance is unsurpassed.

The nuclease resistance of the 2',4'-BNA$^{NC}$-modified oligonucleotide is higher than that of the natural DNA oligonucleotide, but is much lower than that of S-oligo (phosphorothioate type oligonucleotide). The 2',4'-BNA$^{NC}$-modified oligonucleotide of the present invention is superior in nuclease resistance not only to the 2',4'-BNA-modified oligonucleotide, but also to the S-oligo which has been evaluated highly because of its excellent nuclease resistance. Thus, the 2',4'-BNA$^{NC}$-modified oligonucleotide of the present invention has the property of potently resisting degradation in vivo.

(4) The N—O bond contained in the artificial nucleic acid 2',4'-BNA$^{NC}$ molecule of the present invention can be selectively cleaved under mild conditions with the use of a reducing reagent to liberate an NH group and an OH group. Binding of a different functional molecule, with the NH group or the OH group as a foothold, makes it easy to obtain various conjugates, whether before or after preparation of the oligonucleotide analogue. Usable as the different functional group are labeling molecules such as fluorescent molecules, chemiluminescent molecules, and molecular species containing radioisotope atoms, various DNA (RNA) incision activity molecules, and intracellular or nuclear transfer signal peptides.

As described above, the DNA or RNA oligonucleotide analogues of the present invention having 2',4'-BNA$^{NC}$ modified in various forms have very high usefulness not only as highly functional materials for creation of genetic drugs by the antisense method, the antigene method, the decoy method, the genetic homologous recombination method, and the RNA interference method, but also as base materials for genetic diagnosis methods such as molecular beacons and DNA chips, as well as starting materials for the development of research reagents for analysis and elucidation of gene functions.

EMBODIMENTS OF THE INVENTION

Figure 1:
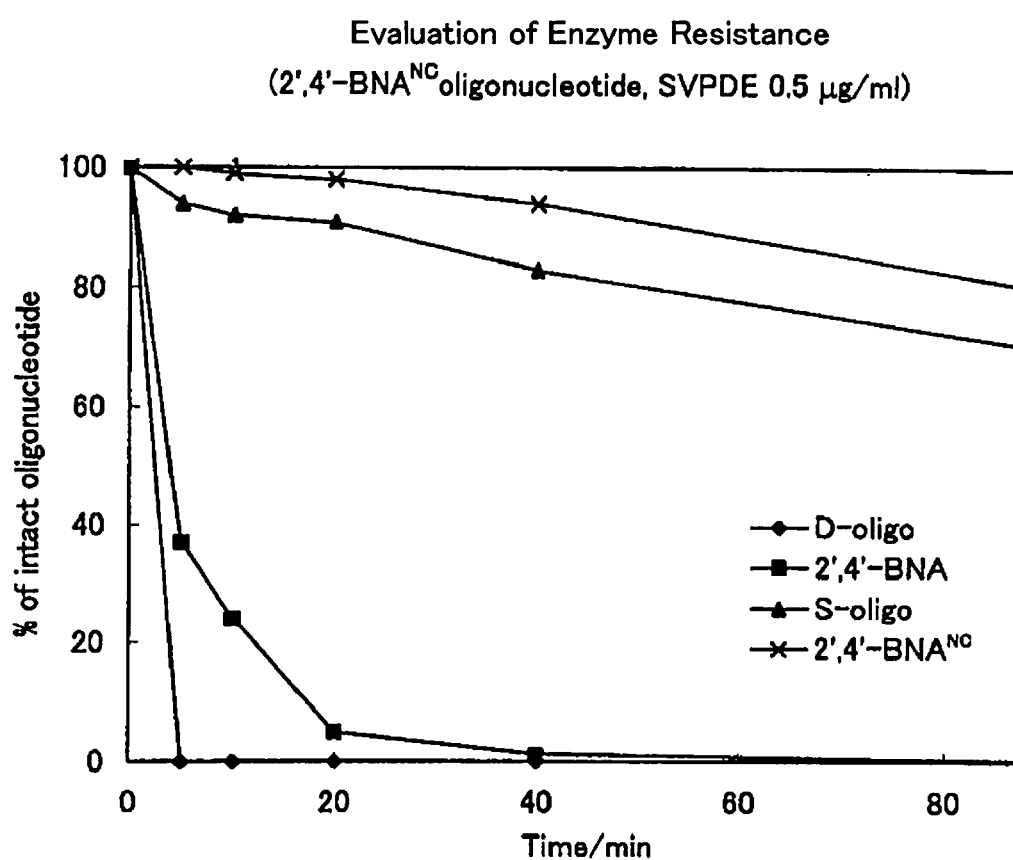
[FIG. 1] A graph showing changes over time in an oligonucleotide analogue (8) of the present invention, and natural and nonnatural oligonucleotide analogues, when degraded by exonuclease, as the survival rates of the undegraded oligonucleotides by HPLC determination.

The nucleoside analogues of the present invention are a compound of the following general formula (I) and a salt thereof.

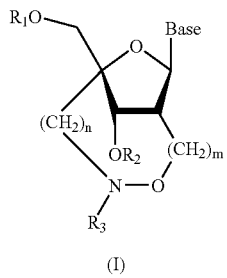

[Chemical Formula 1]

(I)

where Base represents an aromatic heterocyclic group or aromatic hydrocarbon ring group optionally having a substituent, $R_1$ and $R_2$ are identical or different, and each represent a hydrogen atom, a protective group for a hydroxyl group for nucleic acid synthesis, an alkyl group, an alkenyl group, a cycloalkyl group, an aryl group, an aralkyl group, an acyl group, a sulfonyl group, a silyl group, a phosphate group, a phosphate group protected with a protective group for nucleic acid synthesis, or —P($R_4$)$R_5$ [where $R_4$ and $R_5$ are identical or different, and each represent a hydroxyl group, a hydroxyl group protected with a protective group for nucleic acid synthesis, a mercapto group, a mercapto group protected with a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted by an alky group having 1 to 5 carbon atoms, $R_3$ represents a hydrogen atom, an alkyl group, an alkenyl group, a cycloalkyl group, an aryl group, an aralkyl group, an acyl group, a sulfonyl group, or a functional molecule unit substituent, and m denotes an integer of 0 to 2, and n denotes an integer of 1 to 3.

The oligonucleotide analogue of the present invention is a DNA oligonucleotide or RNA oligonucleotide analogue containing one or two or more of any one or more types of unit structures of nucleoside analogues represented by the following general formula (II), or a pharmacologically acceptable salt of the oligonucleotide analogue, provided that if two or more of one or more types of these structures are contained, Base may be identical or different between these structures, and that the bond between the respective nucleosides in the oligonucleotide analogue may contain one or two or more phosphorothioate bonds [—OP(O)(S$^-$)O—] aside from a phosphodiester bond [—OP(O$_2^-$)O—] identical with that in a natural nucleic acid,

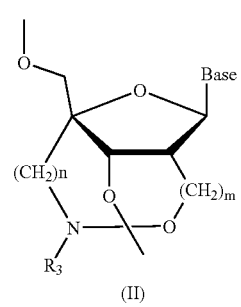

[Chemical Formula 2]

(II)

where Base, $R_1$, $R_2$, $R_3$, m, and n are as defined above.

In the general formulas (I) and (II), the aromatic heterocyclic group as Base refers to any 5-membered to 20-membered ring group which has a structure having the carbon atom, as a constituent atom of a hydrocarbon ring, substituted by one or more hetero-atoms such as nitrogen atoms, sulfur atoms or oxygen atoms, and which shows aromaticity, and includes a single ring or a condensed ring. Its concrete examples are pyrimidine or purine nucleic acid bases, and pyrimidine or purine nucleic acid bases optionally having one or more substituents selected from an α group to be described below. The pyrimidine or purine nucleic acid bases include bases generally known as constituent elements of nucleic acids (for example, guanine, adenine, cytosine, thymine, uracil), and all other chemical structures which are similar to them, and which can act as, or can be used instead of, the bases constituting nucleic acids. Other compounds are also included, such as thiophene, thianthrene, furan, pyran, isobenzofuran, chromene, xanthene, phenoxthine, pyrrole, imidazole, pyrazole, isothiazole, isoxazole, pyridazine, indolizine, indole, isoindole, isoquinoline, quinoline, naphthyridine, quinoxaline, quinazoline, pteridine, carbazole, phenanthridine, acridine, perimidine, phenazine, phenarsazine, phenothiazine, furazane, phenoxazine, pyrrolidine, pyrroline, imidazolidine, imidazoline, and pyrazolidine. Preferred examples are pyrimidine or purine nucleic acid bases, and pyrimidine or purine nucleic acid bases optionally having one or more substituents selected from the α group to be described below. Concretely, a purin-9-yl group, a 2-oxopyrimidin-1-yl group, or a purin-9-yl group or a 2-oxopyrimidin-1-yl group having a substituent selected from the following α group is preferred.

α group: A hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom. A group preferred as "the purine nucleic acid base optionally having the substituent" is a 6-aminopurin-9-yl (i.e. adeninyl) group, a 6-aminopurin-9-yl group having the amino group protected with a protective group for nucleic acid synthesis, a 2,6-diaminopurin-9-yl group, a 2-amino-6-chloropurin-9-yl group, a 2-amino-6-chloropurin-9-yl group having the amino group protected with a protective group for nucleic acid synthesis, a 2-amino-6-fluoropurin-9-yl group, a 2-amino-6-fluoropurin-9-yl group having the amino group protected with a protective group for nucleic acid synthesis, a 2-amino-6-bromopurin-9-yl group, a 2-amino-6-bromopurin-9-yl group having the amino group protected with a protective group for nucleic acid synthesis, a 2-amino-6-hydroxypurin-9-yl (i.e., guaninyl) group, a 2-amino-6-hydroxypurin-9-yl group having the amino group protected with a protective group for nucleic acid synthesis, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloroprolin-2-yl group, or a 6-mercaptopurin-9-yl group. More preferred is a 6-benzoylaminopurin-9-yl group, an adeninyl group, a 2-isobutyrylamino-6-hydroxypurin-9-yl group, or a guaninyl group.

A group preferred as "the pyrimidine nucleic acid base optionally having the substituent" is a 2-oxo-4-amino-1,2-dihydropyrimidin-1-yl (i.e., cytosinyl) group, a 2-oxo-4-amino-1,2-dihydropyrimidin-1-yl group having the amino group protected with a protective group for nucleic acid synthesis, a 2-oxo-4-amino-5-fluoro-1,2-dihydropyrimidin-1-yl group, a 2-oxo-4-amino-5-fluoro-1,2-dihydropyrimidin-1-yl group having the amino group protected with a protective group for nucleic acid synthesis, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e., uracinyl) group, a 2-oxo-4-hydroxy-5-methyl-1,2-dihydropyrimidin-1-yl (i.e., thyminyl) group, or a 4-amino-5-methyl-2-oxo-1,2-dihydropyrimidin-1-yl (i.e., 5-methylcytosinyl) group. More preferred is a 2-oxo-4-benzoylamino-1,2-dihydropyrimidin-1-yl group, a cytosinyl group, a thyminyl group, a uracinyl group, a 2-oxo-4-benzoylamino-5-methyl-1,2-dihydropyrimidin-1-yl group, or a 5-methylcytosinyl group.

More preferred among "the purine or pyrimidine nucleic acid bases optionally having the substituent" is 6-aminopurin-9-yl (i.e. adeninyl), 6-aminopurin-9-yl having the amino group protected with a protective group for nucleic acid synthesis, 2,6-diaminopurin-9-yl group, 2-amino-6-chloropurin-9-yl, 2-amino-6-chloropurin-9-yl having the amino group protected with a protective group for nucleic acid synthesis, 2-amino-6-fluoropurin-9-yl, 2-amino-6-fluoropurin-9-yl having the amino group protected with a protective group for nucleic acid synthesis, 2-amino-6-bromopurin-9-yl, 2-amino-6-bromopurin-9-yl having the amino group protected with a protective group for nucleic acid synthesis, 2-amino-6-hydroxypurin-9-yl (i.e., guaninyl), 2-amino-6-hydroxypurin-9-yl having the amino group protected with a protective group for nucleic acid synthesis, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-2-yl, 6-mercaptopurin-9-yl, 2-oxo-4-amino-1,2-dihydropyrimidin-1-yl (i.e., cytosinyl), 2-oxo-4-amino-1,2-dihydropyrimidin-1-yl having the amino group protected with a protective group for nucleic acid synthesis, 2-oxo-4-amino-5-fluoro-1,2-dihydropyrimidin-1-yl, 2-oxo-4-amino-5-fluoro-1,2-dihydropyrimidin-1-yl having the amino group protected with a protective group for nucleic acid synthesis, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydropyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), or 4-amino-5-methyl-2-oxo-1,2-dihydropyrimidin-1-yl having the amino group protected with a protective group for nucleic acid synthesis.

In the general formulas (I) and (II), the aromatic hydrocarbon ring group as Base refers to a monovalent substituent formed by removing one hydrogen atom from a hydrocarbon ring having 6 to 20 carbon atoms and showing aromaticity, and includes a single ring or a condensed ring. Concrete examples are phenyl, indenyl, naphthyl, pentalenyl, azulenyl, heptalenyl, biphenylenyl, indacenyl, fluorenyl, phenanthryl, and anthryl. Any other structures, which can be used alternatively as the base portion of the nucleic acid component for the purpose of the present invention, are also included in the examples. Moreover, the aromatic hydrocarbon ring may be substituted by one or more groups, such as a hydroxyl group, a hydroxyl group protected with a protective group for nucleic acid synthesis, an amino group, an amino group protected with a protective group for nucleic acid synthesis, a halogen atom, a lower alkyl group, an alkoxy group, a carboxyl group, an aryloxy group, a nitro group, a trifluoromethyl group, and a phenyl group. Examples of such an optionally substituted aromatic hydrocarbon group are 4-hydroxyphenyl, 2-hydroxyphenyl, 4-aminophenyl, 2-aminophenyl, 2-methylphenyl, 2,6-dimethyphenyl, 2-chlorophenyl, 4-chlorophenyl, 2,4-dichlorophenyl, 2,5-dichlorophenyl, 2-bromophenyl, 4-methoxyphenyl, 4-chloro-2-nitrophenyl, 4-nitrophenyl, 2,4-dinitrophenyl, and biphenyl. Preferred examples of the optionally substituted aromatic hydrocarbon ring group are a phenyl group, and a phenyl group substituted by a hydroxyl group, a hydroxyl group protected with a protective group for nucleic acid synthesis, an amino group, an amino group protected with a protective group for nucleic acid synthesis, a lower alkoxy group, or a nitro group.

In the general formula (I) or (II), the "protective group for a hydroxyl group for nucleic acid synthesis" as $R_1$ and $R_2$, and the protective group in the "hydroxyl group protected with a protective group for nucleic acid synthesis" as $R_4$ and $R_5$ and in the α group are not limited, as long as they can protect the hydroxyl group stably during nucleic acid synthesis. Concretely, they refer to protective groups which are stable under acidic or neutral conditions, and which can be cleaved by a chemical method such as hydrogenolysis, hydrolysis, electrolysis, or photolysis. Examples of such protective groups are "aliphatic acyl groups", for example, alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl, carboxylated alkylcarbonyl groups such as succinoyl, glutaroyl, and adipoyl, halogeno lower alkylcarbonyl groups such as chloroacetyl, dichloroacetyl, trichloroacetyl, and trifluoroacetyl, lower alkoxy lower alkylcarbonyl groups such as methoxyacetyl, and unsaturated alkylcarbonyl groups such as (E)-2-methyl-2-butenoyl; "lower alkyl groups" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3,-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl; "lower alkenyl groups" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl; "aromatic acyl groups", for example, arylcarbonyl groups such as benzoyl, α-naphthoyl, and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl, and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-4-yl, and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups", for example, lower trialkylsilyl groups such as trimethylsilyl, triethylsilyl, isopropyldimethylsilyl, t-butyldimethylsilyl, methyldiisopropylsilyl, methyldi-t-butylsilyl, and triisopropylsilyl, lower alkylsilyl groups substituted by one or two aryl groups, such as diphenylmethylsilyl, diphenylbutylsilyl, diphenylisopropylsilyl, and phenyldiisopropylsilyl; "lower alkoxymethyl groups" such as methoxymethyl, 1,1-dimethyl-1-methoxymethyl, ethoxymethyl, propoxymethyl, isopropoxymethyl, butoxymethyl, and tert-butoxymethyl; "lower alkoxylated lower alkoxymethyl groups" such as 2-methoxyethoxymethyl; "halogeno lower alkoxymethyl groups" such as 2,2,2-trichloroethoxymethyl and bis(2-chloroethoxy)methyl; "lower alkoxylated ethyl groups" such as 1-ethoxyethyl and 1-(isopropoxy)ethyl; "halogenated ethyl groups" such as 2,2,2-trichloroethyl; "methyl groups substituted by one to three aryl groups" such as benzyl, α-naphthylmethyl, β-naphthylmethyl, diphenylmethyl, triphenylmethyl, α-naphthyldiphenylmethyl, and 9-anthrylmethyl; "methyl groups substituted by one to three aryl groups having an aryl ring substituted by a lower alkyl, lower alkoxy, halogen, or cyano group", such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl; "lower alkoxycarbonyl groups" such as methoxycarbonyl, ethoxycarbonyl, t-butoxycarbonyl, and isobutoxycarbonyl; "aryl groups substituted by a halogen atom, a lower alkoxy group, or a nitro group", such as 4-chlorophenyl, 2-fluorophenyl, 4-methoxyphenyl, 4-nitrophenyl, and 2,4-dinitrophenyl; "lower alkoxycarbonyl groups substituted by halogen or a lower trialkylsilyl group", such as 2,2,2-trichloroethoxycarbonyl and 2-trimethylsilylethoxycarbonyl; "alkenyloxycarbonyl groups" such as vinyloxycarbonyl and aryloxycarbonyl; and "aralkyloxycarbonyl groups having an aryl ring optionally substituted by one or two lower alkoxy or nitro groups", such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl.

The "protective group for a hydroxyl group for nucleic acid synthesis", as $R_1$ and $R_2$, is preferably the "aliphatic acyl group", the "aromatic acyl group", the "methyl group substituted by one to three aryl groups", the "methyl group substituted by one to three aryl groups having an aryl ring substituted by a lower alkyl, lower alkoxy, halogen, or cyano group", or the "silyl group", more preferably an acetyl group, a benzoyl group, a benzyl group, a p-methoxybenzoyl group, a dimethoxytrityl group, a monomethoxytrityl group, or a tert-butyldiphenylsilyl group. The protective group in the "hydroxyl group protected with a protective group for nucleic acid synthesis", as $R_4$, $R_5$, $R_6$, and $R_7$ and in the α group, is preferably the "aliphatic acyl group", the "aromatic acyl group", the "methyl group substituted by one to three aryl groups", the "aryl group substituted by a halogen atom, a lower alkoxy group, or a nitro group", the "lower alkyl group", or the "lower alkenyl group", more preferably a benzoyl group, a benzyl group, a 2-chlorophenyl group, a 4-chlorophenyl group, or a 2-propenyl group.

In the general formula (I) or (II), the "alkyl group", as $R_1$, $R_2$ and $R_3$, refers to a straight chain or branched chain alkyl group having 1 to 20 carbon atoms, and includes a straight chain or branched chain alkyl group having 1 to 6 carbon atoms (such an alkyl group may herein be referred to as a lower alkyl group), such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3,-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl. The alkyl group also includes a straight chain or branched chain alkyl group having 7 to 20 carbon atoms, such as heptyl, octyl, nonyl or decyl. Preferred is the above-mentioned straight chain or branched chain alkyl group having 1 to 6 carbon atoms.

In the general formula (I) or (II), the "alkenyl group", as $R_1$, $R_2$ and $R_3$, refers to a straight chain or branched chain alkenyl group having 2 to 20 carbon atoms, and includes a straight chain or branched chain alkenyl group having 2 to 6 carbon atoms (such an alkenyl group may herein be referred to as a lower alkenyl group), such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl. The alkeyl group also includes geranyl and farnesyl, and is preferably the above-mentioned straight chain or branched chain alkenyl group having 2 to 6 carbon atoms.

In the general formula (I) or (II), the "cycloalkyl group", as $R_1$, $R_2$ and $R_3$, refers to a cycloalkyl group having 3 to 10 carbon atoms, and includes, for example, cyclopropyl, cyclobutyl, cyclopentyl, cyclohexyl, cycloheptyl, cyclooctyl, norbornyl, and adamantyl. Preferred is a cycloalkyl group having 3 to 8 carbon atoms, such as cyclopropyl, cyclobutyl, cyclopentyl, cyclohexyl, cycloheptyl, or cyclooctyl. The "cycloalkyl group" also includes a heterocyclic group in which one or more methylene groups on the ring of the cycloalkyl group have been substituted by oxygen atoms or sulfur atoms, or nitrogen atoms substituted by an alkyl group. An example of the heterocyclic group is a tetrahydropyranyl group.

In the general formula (I) or (II), the "aryl group", as $R_1$, $R_2$ and $R_3$, refers to a monovalent substituent having 6 to 14 carbon atoms which remains after removing one hydrogen atom from an aromatic hydrocarbon group, and includes, for example, phenyl, indenyl, naphthyl, phenanthrenyl, and anthracenyl. The aryl group may be substituted by one or more groups, such as a halogen atom, a lower alkyl group, a hydroxyl group, an alkoxy group, an aryloxy group, an amino group, a nitro group, trifluoromethyl, and a phenyl group. Examples of the optionally substituted aryl group are 2-methylphenyl, 2,6-dimethylphenyl, 2-chlorophenyl, 4-chlorophenyl, 2,4-dichlorophenyl, 2,5-dichlorophenyl, 2-bromophenyl, 4-methoxyphenyl, 4-chloro-2-nitrophenyl, 4-nitrophenyl, 2,4-dinitrophenyl, and biphenyl. Preferred examples are a phenyl group, and a phenyl group substituted by a halogen atom, a lower alkoxy group, or a nitro group.

In the general formula (I) or (II), the "aralkyl group", as $R_1$, $R_2$ and $R_3$, refers to an alkyl group having 1 to 6 carbon atoms which has been substituted by an aryl group. Examples of the aralkyl group are "methyl groups substituted by one to three aryl groups", such as benzyl, α-naphthylmethyl, β-naphthylmethyl, indenylmethyl, phenanthrenylmethyl, anthracenylmethyl, diphenylmethyl, triphenylmethyl, α-naphthyldiphenylmethyl, and 9-anthrylmethyl, and "methyl groups substituted by one to three aryl groups having an aryl ring substituted by a lower alkyl, lower alkoxy, halogen, or cyano group", such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl. Other examples include "alkyl groups having 3 to 6 carbon atoms substituted by an aryl group", such as 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, and 6-naphthylpentyl. Preferred examples are the "methyl groups substituted by one to three aryl groups", and the "methyl groups substituted by one to three aryl groups having an aryl ring substituted by a lower alkyl, lower alkoxy, halogen, or cyano group". More preferred examples are 4-methoxyphenyldiphenylmethyl, and 4,4'-dimethoxytriphenylmethyl.

Examples of the "acryl group", as $R_1$, $R_2$ and $R_3$, in the general formula (I) or (II) are "aliphatic acyl groups", for example, alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl, carboxylated alkylcarbonyl groups such as succinoyl, glutaroyl, and adipoyl, halogeno lower alkylcarbonyl groups such as chloroacetyl, dichloroacetyl, trichloroacetyl, and trifluoroacetyl, lower alkoxy lower alkylcarbonyl groups such as methoxyacetyl, aryloxy lower alkylcarbonyl groups such as a phenoxyacetyl group, and unsaturated alkylcarbonyl groups such as (E)-2-methyl-2-butenoyl; and "aromatic acyl groups", for example, arylcarbonyl groups such as benzoyl, α-naphthoyl, and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl, and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl. Preferred examples are formyl, acetyl, propionyl, butyryl, isobutyryl, pentanoyl, pivaloyl, benzoyl, and phenoxyacetyl groups.

As the "sulfonyl group", as $R_1$, $R_2$ and $R_3$, in the general formula (I) or (II), there can be named "aliphatic sulfonyl groups", for example, sulfonyl groups substituted by a straight chain or branched chain alkyl group having 1 to 6 carbon atoms, such as methanesulfonyl and ethanesulfonyl, and "aromatic sulfonyl groups", for example, sulfonyl groups substituted by various aryl groups, such as benzenesulfonyl and p-toluenesulfonyl. Preferred examples are methanesulfonyl and p-toluenesulfonyl.

As the "silyl group", as $R_1$, $R_2$ and $R_3$, in the general formula (I) or (II), there can be named "lower trialkylsilyl groups" such as trimethylsilyl, triethylsilyl, isopropyldimethylsilyl, tert-butyldimethylsilyl, methyldiisopropylsilyl, methyldi-tert-butylsilyl, and triisopropylsilyl, "lower alkylsilyl groups substituted by one or two aryl groups", such as diphenylmethylsilyl, tert-butyldiphenylbutylsilyl, diphenylisopropylsilyl, and phenyldiisopropylsilyl. Preferred examples are trimethylsilyl, triethylsilyl, triisopropylsilyl, t-butyldimethylsilyl, t-butyldiphenylsilyl. A more preferred example is trimethylsilyl.

In the general formula (I) or (II), the "protective group" in the "phosphate group protected with a protective group for nucleic acid synthesis" as $R_1$ and $R_2$ is not limited, as long as it can protect the phosphate group stably during nucleic acid synthesis. Concretely, it refers to a protective group which is stable under acidic or neutral conditions, and which can be cleaved by a chemical method such as hydrogenolysis, hydrolysis, electrolysis, or photolysis. Examples of such a protective group are "lower alkyl groups" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3,-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl; "cyanated lower alkyl groups" such as 2-cyanoethyl, and 2-cyano-1,1-dimethylethyl; "ethyl groups substituted by a silyl group", such as 2-methyldiphenylsilylethyl, 2-trimethylsilylethyl, and 2-triphenylsilylethyl; "halogenated lower alkyl groups", such as 2,2,2-trichloroethyl, 2,2,2-tribromoethyl, 2,2,2-trifluoroethyl, and 2,2,2-trichloro-1,1-diemthylethyl; "lower alkenyl groups", such as ethenyl, 1-propenyl, 2-propenyl, 1-methyl-2-propenyl, 1-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl; "cycloalkyl groups", such as cyclopropyl, cyclobutyl, cyclopentyl, cyclohexyl, cycloheptyl, norbornyl, and adamantyl; "cyanated lower alkenyl groups" such as 2-cyanobutenyl; "aralkyl groups", such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, and 6-naphthylpentyl; "aralkyl groups having an aryl ring substituted by a nitro group or a halogen atom", such as 4-chlorobenzyl, 2-(4-nitrophenyl)ethyl, o-nitrobenzyl, 4-nitrobenzyl, 2,4-dinitrobenzyl, and 4-chloro-2-nitrobenzyl; "aryl groups", such as phenyl, indenyl, naphthyl, phenanthrenyl, and anthracenyl; and "aryl groups substituted by a lower alkyl group, a halogen atom, or a nitro group", such as 2-methylphenyl, 2,6-dimethylphenyl, 2-chlorophenyl, 4-chlorophenyl, 2,4-dichlorophenl, 2,5-dichlorophenyl, 2-bromophenyl, 4-nitrophenyl, and 4-chloro-2-nitrophenyl. Preferred examples are the "lower alkyl groups", "lower alkyl groups substituted by a cyano group", "aralkyl groups", "aralkyl groups having an aryl ring substituted by a nitro group or a halogen atom", or "aryl groups substituted by a lower alkyl group, a halogen atom, or a nitro group". A more preferred example is a 2-cyanoethyl group, a 2,2,2-trichloroethyl group, a benzyl group, a 2-chlorophenyl group, or a 4-chlorophenyl group.

In the general formula (I) or (II), the "functional molecule unit substituent" as $R_3$ includes labeling molecules (for example, fluorescent molecules, chemiluminescent molecules, and molecular species containing radioisotope atoms), DNA or RNA incision activity molecules, and intracellular or nuclear transfer signal peptides.

In the general formula (I) or (II), the protective group in "the mercapto group protected with a protective group for nucleic acid synthesis" as $R_4$ and $R_5$ and in the α group is not limited, as long as it can protect the mercapto group stably during nucleic acid synthesis. Concretely, it refers to a protective group which is stable under acidic or neutral conditions, and which can be cleaved by a chemical method such as hydrogenolysis, hydrolysis, electrolysis, or photolysis. Examples of such a protective group are those named above as the protective group for the hydroxyl group, as well as "disulfide-forming groups", for example, alkylthio groups such as methylthio, ethylthio, and tert-butylthio, and arylthio groups such as benzylthio. Preferred examples are "aliphatic acyl groups" or "aromatic acyl groups". More preferred examples are a benzoyl group and a benzyl group.

Examples of "the alkoxy group having 1 to 5 carbon atoms" as $R_4$ and $R_5$ and in the α group in the general formula (I) or (II) are methoxy, ethoxy, n-propoxy, isopropoxy, n-butoxy, isobutoxy, s-butoxy, tert-butoxy, and n-pentoxy. A preferred example is a methoxy or ethoxy group.

Examples of "the alkylthio group having 1 to 5 carbon atoms" as $R_4$ and $R_5$ and in the α group in the general formula (I) or (II) are methylthio, ethylthio, propylthio, isopropylthio, butylthio, isobutylthio, s-butylthio, tert-butylthio, and n-pentylthio. A preferred example is a methylthio or ethylthio group.

Examples of "the cyanoalkoxy group having 1 to 6 carbon atoms" as $R_4$ and $R_5$ in the general formula (I) or (II) are the above "alkoxy groups having 1 to 5 carbon atoms" which have been substituted by a cyano group. Such groups are, for example, cyanomethoxy, 2-cyanoethoxy, 3-cyanopropoxy, 4-cyanobutoxy, 3-cyano-2-methylpropoxy, and 1-cyanomethyl-1,1-dimethylmethoxy. A preferred example is a 2-cyanoethoxy group.

Examples of "the amino group substituted by an alkyl group having 1 to 5 carbon atoms", as $R_4$ and $R_5$ and in the α group in the general formula (I) or (II), are methylamino, ethylamino, propylamino, isopropylamino, butylamino, isobutylamino, s-butylamino, tert-butylamino, dimethylamino, diethylamino, dipropylamino, diisopropylamino, dibutylamino, diisobutylamino, di(s-butyl)amino, and di(tert-butyl)amino. A preferred example is methylamino, ethylamino, dimethylamino, diethylamino, or diisopropylamino group.

As the "alkyl group having 1 to 5 carbon atoms" in the α group, there can be named, for example, methyl, ethyl, propyl, isopropyl, butyl, isobutyl, s-butyl, tert-butyl, and n-pentyl. A preferred example is a methyl or ethyl group.

As the "halogen atom" in the α group, there can be named, for example, a fluorine atom, a chlorine atom, a bromine atom, and an iodine atom, A preferred example is a fluorine atom or a chlorine atom.

The "phosphoroamidite group" refers to a group of the formula $-P(OR_{1a})(NR_{1b})$ (where $R_{1a}$ represents an alkyl group having 1 or more carbon atoms or a cyanoalkyl group having 1 to 7 carbon atoms, and $R_{1b}$ represents an alkyl group having 1 to 6 carbon atoms). A preferred example is α group of the formula $-P(OC_2H_4CN)(N(i-Pr)_2)$ or a group of the formula $-P(OCH_3)(N(i-Pr)_2)$.

The protective group in the "amino group protected with a protective group for nucleic acid synthesis" in the α group is not limited, as long as it can protect the amino group stably during nucleic acid synthesis. Concretely, it refers to a protective group which is stable under acidic or neutral conditions, and which can be cleaved by a chemical method such as hydrogenolysis, hydrolysis, electrolysis, or photolysis. Examples of such a protective group are "aliphatic acyl groups", for example, alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, nonadecanoyl, eicosanoyl, and heneicosanoyl, carboxylated alkylcarbonyl groups such as succinoyl, glutaroyl, and adipoyl, halogeno lower alkylcarbonyl groups such as chloroacetyl, dichloroacetyl, trichloroacetyl, and trifluoroacetyl, lower alkoxy lower alkylcarbonyl groups such as methoxyacetyl, and unsaturated alkylcarbonyl groups such as (E)-2-methyl-2-butenoyl; "aromatic acyl groups", for example, arylcarbonyl groups such as benzoyl, α-naphthoyl, and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl, and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl; "lower alkoxycarbonyl groups" such as methoxycarbonyl, ethoxycarbonyl, t-butoxycarbonyl, and isobutoxycarbonyl; "lower alkoxycarbonyl groups substituted by halogen or a lower trialkylsilyl group", such as 2,2,2-trichloroethoxycarbonyl and 2-trimethylsilylethoxycarbonyl; "alkenyloxycarbonyl groups" such as vinyloxycarbonyl and aryloxycarbonyl; and "aralkyloxycarbonyl groups having an aryl ring optionally substituted by one or two lower alkoxy or nitro groups", such as benzyloxycarbonyl, 4-methoxybenzyloxycarbonyl, 2-nitrobenzyloxycarbonyl, and 4-nitrobenzyloxycarbonyl. A preferred example is the "aliphatic acyl group" or "aromatic acyl group", and a more preferred example is a benzoyl group.

The "nucleoside analogue" refers to a nonnatural type of "nucleoside" consisting of a purine or pyrimidine base and a sugar linked together, or a product consisting of an aromatic heterocyclic ring or an aromatic hydrocarbon ring, which is other than purine and pyrimidine and which can be used instead of the purine or pyrimidine base, and a sugar linked together.

The "oligonucleotide analogue" refers to a nonnatural type derivative of "oligonucleotide" comprising 2 to 50 identical or different "nucleosides" or "nucleoside analogues" linked together by phosphodiester bonds. Preferred examples of such an analogue are sugar derivatives with the sugar portion modified; thioate derivatives formed upon thioation of the phosphodiester portion; esters formed upon esterification of the terminal phosphoric acid portion; and amides formed upon amidation of the amino group on the purine base. More preferred examples are sugar derivatives with the sugar portion modified.

The "salt thereof" refers to a salt of the compound (1) of the present invention, because the compound (1) can be converted into the salt. Preferred examples of the salt are metal salts, for example, alkali metal salts such as sodium salt, potassium salt, and lithium salt, alkaline earth metal salts such as calcium salt and magnesium salt, aluminum salt, iron salt, zinc salt, copper salt, nickel salt, and cobalt salt; amine salts, for example, inorganic salts such as ammonium salt, and organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, and tris(hydroxymethyl)aminomethane salt; inorganic acid salts, for example, halogenated hydroacid salts such as hydrofluoride, hydrochloride, hydrobromide, and hydriodide, nitrate, perchlorate, sulfate, and phosphate; organic acid salts, for example, lower alkanesulfonates such as methanesulfonate, trifluoromethanesulfonate, and ethanesulfonate, arylsulfonates such as benzenesulfonate and p-toluenesulfonate, acetate, malate, fumarate, succinate, citrate, tartrate, oxalate, and maleate; and amino acid salts such as glycine salt, lysine salt, arginine salt, ornithine salt, glutamate, and aspartate.

The "pharmacologically acceptable salt thereof" refers to a salt of the oligonucleotide analogue of the present invention, because the oligonucleotide can be converted into the salt. Preferred examples of the salt are metal salts, for example, alkali metal salts such as sodium salt, potassium salt, and lithium salt, alkaline earth metal salts such as calcium salt and magnesium salt, aluminum salt, iron salt, zinc salt, copper salt, nickel salt, and cobalt salt; amine salts, for example, inorganic salts such as ammonium salt, and organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, and tris(hydroxymethyl)aminomethane salt; inorganic acid salts, for example, halogenated hydroacid salts such as hydrofluoride, hydrochloride, hydrobromide, and hydriodide, nitrate, perchlorate, sulfate, and phosphate; organic acid salts, for example, lower alkanesulfonates such as methanesulfonate, trifluoromethanesulfonate, and ethanesulfonate, arylsulfonates such as benzenesulfonate and p-toluenesulfonate, acetate, malate, fumarate, succinate, citrate, tartrate, oxalate, and maleate; and amino acid salts such as glycine salt, lysine salt, arginine salt, ornithine salt, glutamate, and aspartate.

Of the compounds (I) of the present invention and the salts thereof, preferred compounds are as follows:

(1) Compounds and salts thereof, with $R_1$ being a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, or a silyl group.

(2) Compounds and salts thereof, with $R_1$ being a hydrogen atom, an acetyl group, a benzoyl group, a methanesulfonyl group, a p-toluenesulfonyl group, a benzyl group, a p-methoxybenzyl group, a trityl group, a dimethoxytrityl group, a monomethoxytrityl group, or a tert-butyldiphenylsilyl group.

(3) Compounds and salts thereof, with $R_2$ being a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, a silyl group, a phosphoroamidite group, a phosphonyl group, a phosphate group, or a phosphate group protected with a protective group for nucleic acid synthesis.

(4) Compounds and salts thereof, with $R_2$ being a hydrogen atom, an acetyl group, a benzoyl group, a methanesulfonyl group, a p-toluenesulfonyl group, a benzyl group, a p-methoxybenzyl group, a tert-butyldiphenylsilyl group, —P(OC$_2$H$_4$CN)(N(i-Pr)$_2$), —P(OCH$_3$)(N(i-Pr)$_2$), a phosphonyl group, or a 2-chlorophenyl- or 4-chlorophenylphosphate group.

(5) Compounds and salts thereof, with R$_3$ being a hydrogen atom, an alkyl group having 1 to 5 carbon atoms, an alkenyl group having 1 to 5 carbon atoms, an aryl group having 6 to 14 carbon atoms, a methyl group substituted by one to three aryl groups, a lower aliphatic or aromatic sulfonyl group such as a methanesulfonyl group or a p-toluenesulfonyl group, an aliphatic acyl group having 1 to 5 carbon atoms such as an acetyl group, or an aromatic acyl group such as a phenoxyacetyl group or a benzoyl group; or the compounds and salts thereof according to any one of claims 1 to 6, with the functional molecule unit substituent as R$_3$ being a fluorescent or chemiluminescent labeling molecule, a nucleic acid incision activity functional group, or an intracellular or nuclear transfer signal peptide.

(6) Compounds and salts thereof, with Base being a 6-aminopurin-9-yl (i.e. adeninyl) group, a 6-aminopurin-9-yl group having the amino group protected with a protective group for nucleic acid synthesis, a 2,6-diaminopurin-9-yl group, a 2-amino-6-chloropurin-9-yl group, a 2-amino-6-chloropurin-9-yl group having the amino group protected with a protective group for nucleic acid synthesis, a 2-amino-6-fluoropurin-9-yl group, a 2-amino-6-fluoropurin-9-yl group having the amino group protected with a protective group for nucleic acid synthesis, a 2-amino-6-bromopurin-9-yl group, a 2-amino-6-bromopurin-9-yl group having the amino group protected with a protective group for nucleic acid synthesis, a 2-amino-6-hydroxypurin-9-yl (i.e., guaninyl) group, a 2-amino-6-hydroxypurin-9-yl group having the amino group protected with a protective group for nucleic acid synthesis, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl (i.e., cytosinyl) group, a 2-oxo-4-amino-1,2-dihydropyrimidin-1-yl group having the amino group protected with a protective group for nucleic acid synthesis, a 2-oxo-4-amino-5-fluoro-1,2-dihydropyrimidin-1-yl group, a 2-oxo-4-amino-5-fluoro-1,2-dihydropyrimidin-1-yl group having the amino group protected with a protective group for nucleic acid synthesis, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e., uracinyl) group, a 2-oxo-4-hydroxy-5-methyl-1,2-dihydropyrimidin-1-yl (i.e., thyminyl) group, a 4-amino-5-methyl-2-oxo-1,2-dihydropyrimidin-1-yl (i.e., 5-methylcytosinyl) group, or 4-amino-5-methyl-2-oxo-1,2-dihydropyrimidin-1-yl having the amino group protected with a protective group for nucleic acid synthesis.

(7) There can also be named compounds and salts thereof, with Base being a benzoylaminopurin-9-yl, adenyl, 2-isobutyrylamino-6-hydroxypurin-9-yl, guaninyl, 2-oxo-4-benzoylamino-1,2-dihydropyrimidin-1-yl, cytosinyl, 2-oxo-5-methyl-4-benzoylamino-1,2-dihydropyrimidin-1-yl, 5-methylcytosinyl, uracinyl, or thyminyl group.

The above (1) to (2), (3) to (4), or (6) to (7) represent more preferred compounds, as their numbers grow. Also preferred are compounds and salts thereof in which, in the general formula (1), R$_1$ is arbitrarily selected from (1) to (2), R$_2$ is arbitrarily selected from (3) to (4), R$_3$ is arbitrarily selected from (5), and Base is arbitrarily selected from (6) to (7); or compounds and salts thereof obtained by arbitrary combinations of these numbers. Particularly preferred combinations are (2)-(3)-(5)-(6), (2)-(3)-(5)-(7), (2)-(4)-(5)-(6), and (2)-(4)-(5)-(7).

There are named compounds of the general formula (I) and salts thereof, particularly preferably, compounds of the following formula and salts thereof.

[Chemical Formula 3]

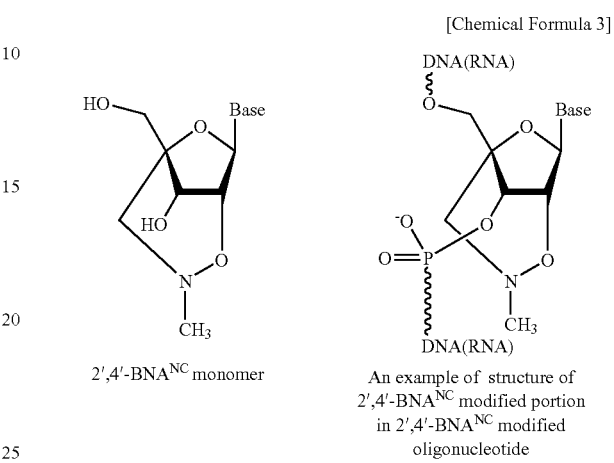

2',4'-BNA$^{NC}$ monomer

An example of structure of 2',4'-BNA$^{NC}$ modified portion in 2',4'-BNA$^{NC}$ modified oligonucleotide In the structural formula of the above group, Base has the same meanings as offered above.

Of the oligonucleotide analogues containing one or two or more unit structures of the nucleoside analogue represented by the general formula (II) of the present invention, and pharmacologically acceptable salts thereof, preferred examples are as follows:

(8) Oligonucleotide analogues, and pharmacologically acceptable salts thereof, with R$_3$ being a hydrogen atom, an alkyl group having 1 to 5 carbon atoms, an aralkyl group such as a benzyl group, an aliphatic or aromatic acyl group such as an acetyl group or a benzoyl group, or an aliphatic or aromatic sulfonyl group such as a methanesulfonyl group or a p-toluenesulfonyl group, (9) Oligonucleotide analogues, and pharmacologically acceptable salts thereof, with Base being a 6-aminopurin-9-yl (i.e. adeninyl) group, a 6-aminopurin-9-yl group having the amino group protected with a protective group for nucleic acid synthesis, a 2,6-diaminopurin-9-yl group, a 2-amino-6-chloropurin-9-yl group, a 2-amino-6-chloropurin-9-yl group having the amino group protected with a protective group for nucleic acid synthesis, a 2-amino-6-fluoropurin-9-yl group, a 2-amino-6-fluoropurin-9-yl group having the amino group protected with a protective group for nucleic acid synthesis, a 2-amino-6-bromopurin-9-yl group, a 2-amino-6-bromopurin-9-yl group having the amino group protected with a protective group for nucleic acid synthesis, a 2-amino-6-hydroxypurin-9-yl (i.e., guaninyl) group, a 2-amino-6-hydroxypurin-9-yl group having the amino group protected with a protective group for nucleic acid synthesis, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl (i.e., cytosinyl) group, a 2-oxo-4-amino-1,2-dihydropyrimidin-1-yl group having the amino group protected with a protective group for nucleic acid synthesis, a 2-oxo-4-amino-5-fluoro-1,2-dihydropyrimidin-1-yl group, a 2-oxo-4-amino-5-fluoro-1,2-dihydropyrimidin-1-yl group having the amino group protected with a protective group for nucleic acid synthesis, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e., uracinyl) group, a 2-oxo-4-hydroxy-5-methyl-1,2-dihydropyrimidin-1-yl (i.e., thyminyl) group, a 4-amino-5-methyl-2-oxo-1,2-dihydropyrimidin-1-yl (i.e., 5-methylcytosinyl) group, or 4-amino-5-methyl-2-oxo-1,2-dihydropyrimidin-1-yl having the amino group protected with a protective group for nucleic acid synthesis.

(10) There can also be named oligonucleotide analogues, and pharmacologically acceptable salts thereof, with Base being a benzoylaminopurin-9-yl, adenyl, 2-isobutyrylamino-6-hydroxypurin-9-yl, guaninyl, 2-oxo-4-benzoylamino-1,2-dihydropyrimidin-1-yl, cytosinyl, 2-oxo-5-methyl-4-benzoylamino-1,2-dihydropyrimidin-1-yl, 5-methylcytosinyl, uracinyl, or thyminyl group.

The above (9) to (10) represent more preferred oligonucleotide analogues, as their numbers grow. Also preferred are oligonucleotide analogues and pharmacologically acceptable salts thereof in which $R_3$ is arbitrarily selected from (8), Base is arbitrarily selected from (9) to (10), and the selected $R_3$ and Base are arbitrarily combined. Particularly preferred combinations in the general formula (II) are (8)-(9) and (8)-(10).

The nucleoside analogues and oligonucleotide analogues of the present invention can be synthesized based on the methods described in the Examples offered herein, and the conventional technologies in the field of the art.

(1) Synthesis of Nucleoside Analogues

Compounds represented by the general formula (I) can be synthesized based on the methods described in the Examples and the conventional technologies in the field of the art. The reaction conditions, reagents for introduction of a protective group, and reaction reagents can be determined with reference to the methods described in the Examples. However, these methods are not limitative, and reaction conditions and reagents usable based on common knowledge in the field of the art can be employed as appropriate. For example, the methods described in Japanese Patent Application Laid-Open No. 2000-297097 and Japanese Patent Application Laid-Open No. 1998-304889 can be referred to. Moreover, if the compounds of the general formula (I) or (II) have various natural or nonnatural nucleic acid bases or other aromatic heterocyclic rings or aromatic hydrocarbon rings as Base, the starting materials for the compounds of the present invention can be synthesized with reference to the methods described in Japanese Patent Application Laid-Open No. 1998-304889.

(2) Synthesis of Oligonucleotide Analogues

The oligonucleotide analogue containing the nucleoside analogue of the present invention can be synthesized in various forms by a publicly known DNA synthesizer. Then, the resulting oligonucleotide analogue is purified by use of a reversed phase column, and the purity of the product is analyzed by reversed phase HPLC or MALDI-TOF-MS, whereby the formation of a purified oligonucleotide analogue can be confirmed.

One or more of the nucleoside analogues of the present invention can be rendered present in the oligonucleotide analogue. Furthermore, the nucleoside analogues may be rendered present at two or more locations of the oligonucleotide analogue in spaced state via one or two or more natural nucleotides. According to the present invention, it is possible to synthesize an oligonucleotide analogue in which the nucleoside analogues of the present invention have been introduced in necessary numbers (length) at necessary positions. The length of the entire oligonucleotide analogue is 2 to 50, preferably 8 to 30 nucleotide units.

The oligonucleotide analogue of the present invention is minimally degradable by nuclease and, following administration in vivo, can exist in vivo for a long period. The oligonucleotide analogue forms a duplex with sense RNA, for example, to inhibit the transcription of an etiological in vivo component (protein) to mRNA. The oligonucleotide analogue is also considered to inhibit the multiplication of an infecting virus.

In the light of these facts, the oligonucleotide analogues of the present invention can be expected to be useful as medicines, including antitumor agents and antiviral agents, for inhibiting the actions of genes to treat diseases. That is, according to the present invention, there are provided oligonucleotide analogues, which have stable and excellent antisense or antigene activity or have excellent activities as reagents for detection of particular genes, or as primers for initiation of amplification, or nucleoside analogues which are intermediates for production of the oligonucleotide analogues.

DNA or RNA oligonucleotide analogues (oligonucleotide analogues), which have the 2',4'-BNA$^{NC}$ monomer, as one of the nucleoside analogues of the present invention, modified in various forms, are useful as materials for various physiological and bioactive substances and pharmaceuticals, functional materials for double-stranded oligonucleotides for the RNA interference method or decoy method, functional materials for DNA chips or molecular beacons targeting single-stranded nucleic acids such as cDNA, functional materials for applications to various antisense methods (including ribozymes and DNAzymes), antigene method, and genetic homologous recombination, materials for high sensitivity analysis of biological trace components by combinations with fluorescent or luminescent substances, and starting materials for the development of research reagents for analysis and elucidation of gene functions.

The nucleoside analogues or oligonucleotide analogues of the present invention can be formed into preparations for parenteral administration by incorporating therein customary adjuvants such as buffers and/or stabilizers. For use as preparations for topical administration, customary pharmaceutical carriers are incorporated, whereby the nucleoside analogues or oligonucleotide analogues can be formed into ointments, creams, liquids and solution, or plasters.

The nucleoside analogues and oligonucleotide analogues of the present invention were synthesized in accordance with the synthesis scheme shown below. These syntheses will be described in further detail in the Examples. Compounds 16, 21, 17 and 22 are amidites for introducing 2',4'-BNA$^{NC}$ (NMe) and 2',4'-BNA$^{NC}$(NH), in which the nucleic acid base portions are thymine and methylcytosine, respectively, into oligonucleotides. From compound 28 as well, amidite 29 for introduction of a methylcytidine BNA$^{NC}$(NH) derivative can be synthesized in the usual manner (tritylation, amiditation). Derivatives of Compound 1, in which the nucleic acid base portions are adenine and guanine instead of thymine, are also known. Thus, adenosine and guanosine 2',4'-BNA$^{NC}$ derivatives are also considered to be synthesizable by this synthesis route.

EXAMPLES

The nucleoside analogues and oligonucleotide analogues of the present invention were synthesized in accordance with the synthesis scheme offered below. These syntheses will be described in further detail in the Examples. The characteristics of the synthesized oligonucleotide analogues were measured by Experimental Examples.

Synthesis
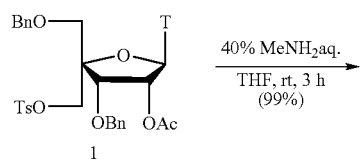
40% MeNH₂aq.
THF, rt, 3 h
(99%)
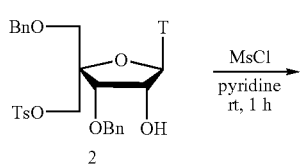
MsCl
pyridine
rt, 1 h
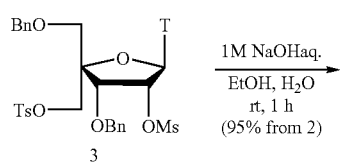
1M NaOHaq.
EtOH, H₂O
rt, 1 h
(95% from 2)
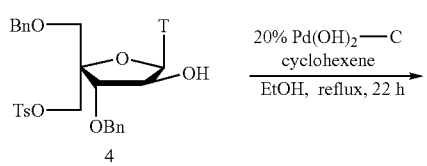
20% Pd(OH)₂—C
cyclohexene
EtOH, reflux, 22 h
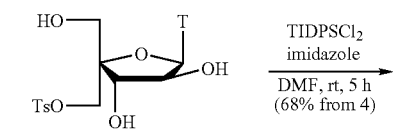
TIDPSCl₂
imidazole
DMF, rt, 5 h
(68% from 4)
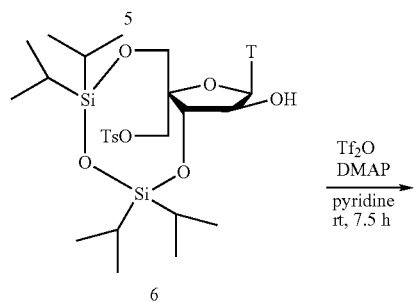
Tf₂O
DMAP
pyridine
rt, 7.5 h
[Chemical Formula 4]
-continued
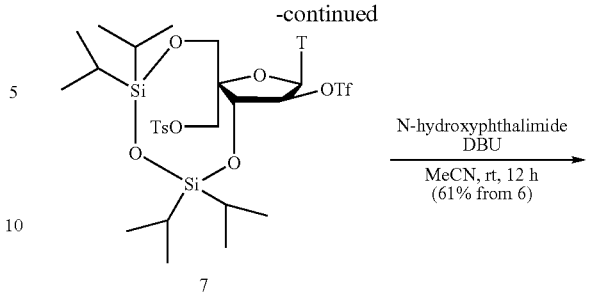
N-hydroxyphthalimide
DBU
MeCN, rt, 12 h
(61% from 6)
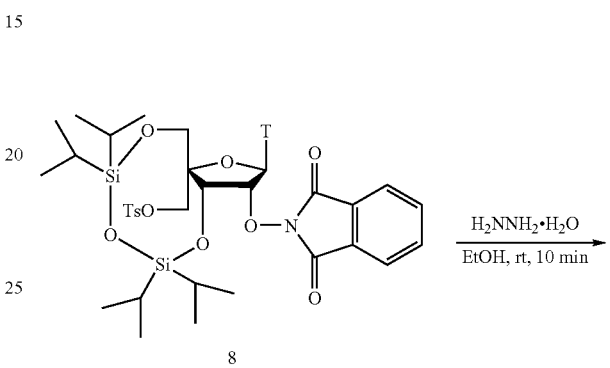
H₂NNH₂·H₂O
EtOH, rt, 10 min
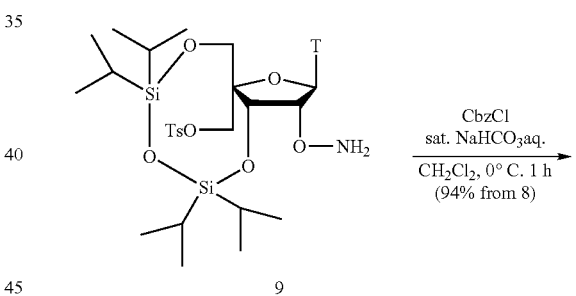
CbzCl
sat. NaHCO₃aq.
CH₂Cl₂, 0° C. 1 h
(94% from 8)
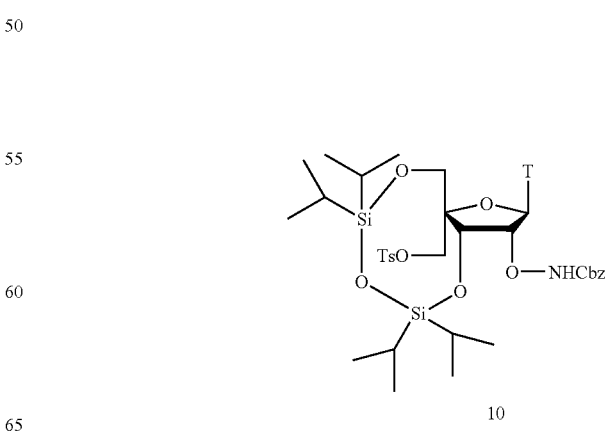

[Chemical Formula 5]
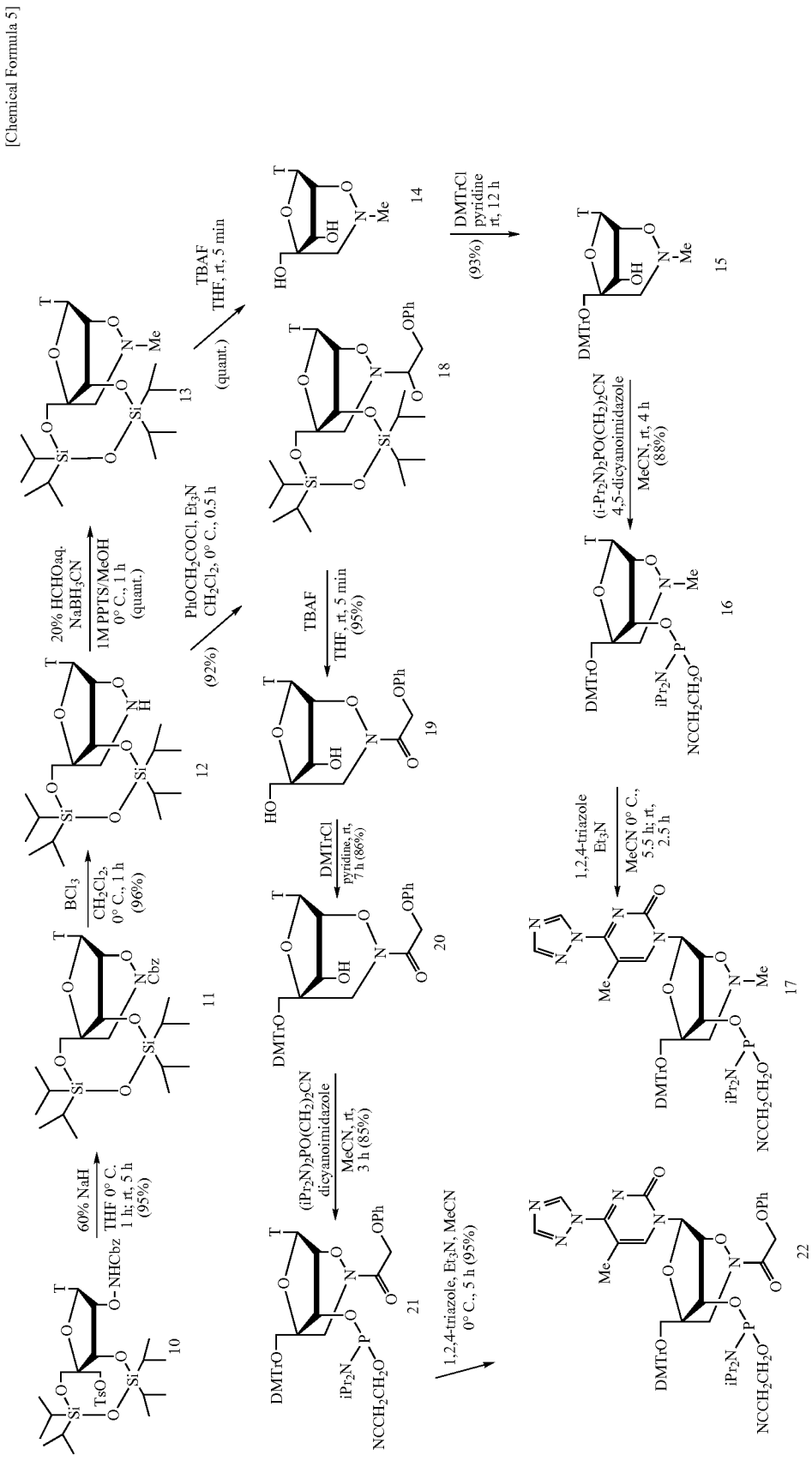

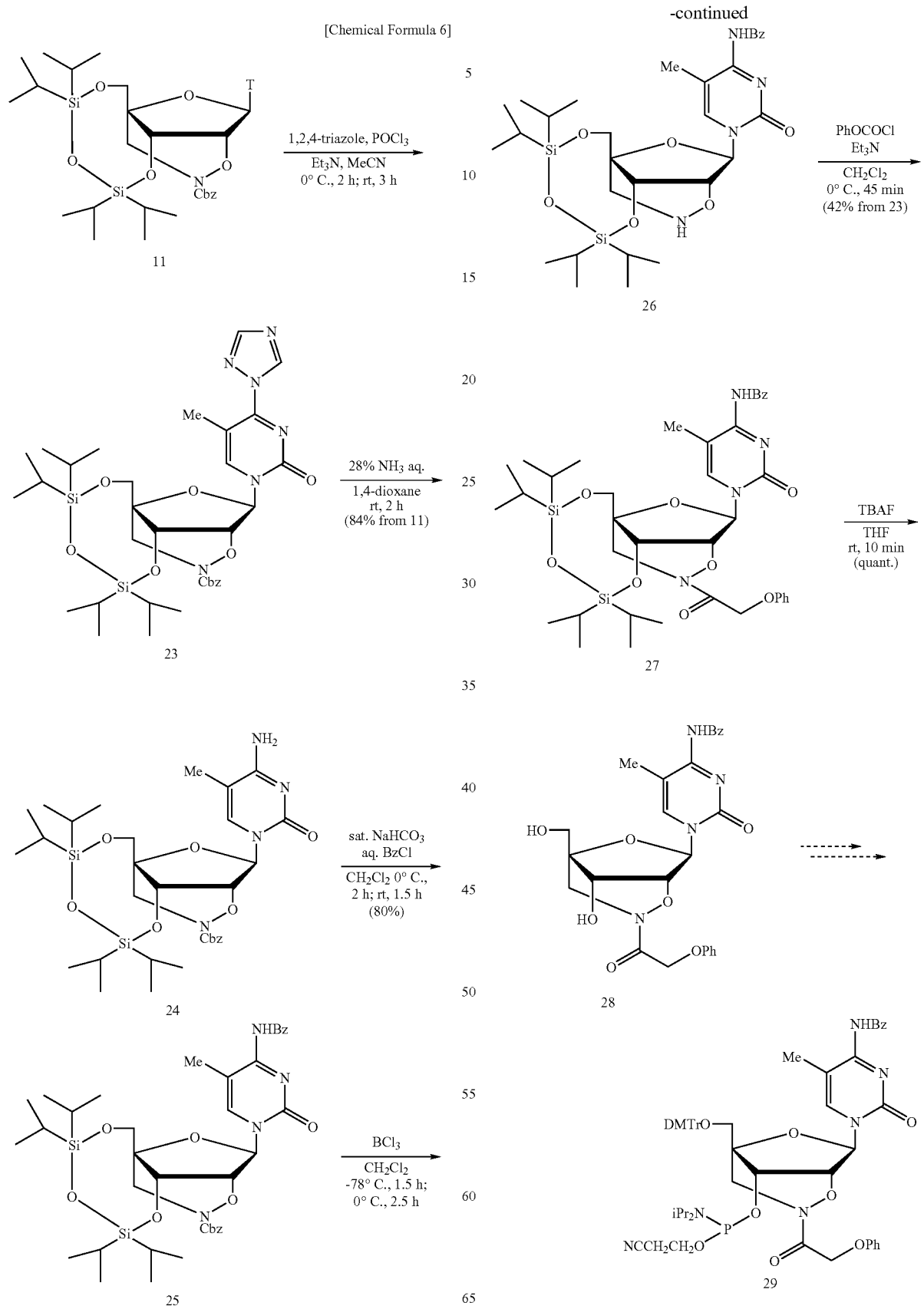

Example 1

Synthesis of Nucleoside Analogues (2',4'-BNA$^{NC}$ Amidites)

(1) Synthesis of Compound 2

A 40% aqueous solution of methylamine (0.11 ml, 1.50 mmols) was added to a tetrahydrofuran solution (3.5 ml) of Compound 1 (49 mg, 0.073 mmol) shown in the above synthesis scheme under ice-cooled conditions, and the mixture was stirred for 3 hours at room temperature. After the solvent of the reaction solution was distilled off, the residue was extracted with ethyl acetate, and the organic layer was washed with water and a saturated aqueous solution of sodium chloride. The organic layer was dried over anhydrous sodium sulfate, and the solvent was distilled off. Then, the residue was purified by silica gel column chromatography (n-hexane: ethyl acetate=1:1) to obtain Compound 2 (45 mg, 99%) as a white solid.

[Equation 1]

mp 64-66° C. $^1$H-NMR (CDCl$_3$) δ: 1.62 (3H, s), 2.43 (3H, s), 3.10 (1H, br), 3.63, 3.71 (2H, AB, J=10 Hz), 4.18 (2H, s), 4.24 (1H, d, J=6 Hz), 4.33 (1H, dd, J=5, 6 Hz), 4.52 (1H, s), 4.60, 4.67 (2H, AB, J=12 Hz), 5.68 (1H, d, J=5 Hz), 7.23-7.37 (13H, m), 7.71 (2H, d, J=8 Hz), 8.52 (1H, br).

(2) Synthesis of Compound 3

In a stream of nitrogen, methylsulfonyl chloride (45 ml, 0.59 mmol) was added to a pyridine solution (1.5 ml) of Compound 2 (146 mg, 0.23 mmol) under ice-cooled conditions, and the mixture was stirred for 1 hour at room temperature. Water was added to the reaction solution, and the mixture was extracted with ethyl acetate. The organic layer was washed with a saturated aqueous solution of sodium bicarbonate, and a saturated aqueous solution of sodium chloride. Then, the organic layer was dried over anhydrous sodium sulfate. The solvent was distilled off under reduced pressure, and the resulting crude product 3 (170 mg) was used for a next reaction without being purified.

[Equation 2]

$^1$H-NMR (CDCl$_3$) δ: 1.65 (3H, s), 2.43 (3H, s), 3.07 (3H, s), 3.55, 3.81 (2H, AB, J=10 Hz), 4.13, 4.22 (2H, AB, J=11 Hz), 4.41 (1H, d, J=6 Hz), 4.48 (2H, s), 4.48, 4.78 (2H, AB, J=12 Hz), 5.32 (1H, dd, J=4, 6 Hz), 5.91 (1H, d, J=4 Hz), 7.20-7.38 (13H, m), 7.72 (2H, d, J=6 Hz).

(3) Synthesis of Compound 4

A 1M aqueous solution of sodium hydroxide (0.70 ml, 0.70 mmol) was added, at room temperature, to a water-ethanol solution (1:2, 6 ml) of the crude product 3 (170 mg) obtained in the preceding reaction, and the mixture was stirred for 1 hour. After neutralization with a 10% aqueous solution of hydrochloric acid, the mixture was extracted with ethyl acetate. The organic layer was washed with water and a saturated aqueous solution of sodium chloride, and then dried over anhydrous sodium sulfate. The solvent was distilled off under reduced pressure, and the resulting crude product was purified by silica gel column chromatography (chloroform: methanol=15:1) to obtain Compound 4 (139 mg, 95% from 2 in 2 steps) as a white solid.

[Equation 3]

mp 73-76° C. $^1$H-NMR (CDCl$_3$) δ: 1.65 (3H, s), 2.38 (3H, B), 3.64, 3.70 (2H, AB, J=9 Hz), 4.12 (1H, d, J=2 Hz), 4.15, 4.21 (2H, AB, J=10 Hz), 4.43, 4.64 (2H, AB, J=11 Hz), 4.49 (2H, s), 4.55 (1H, dd, J=2, 4 Hz), 5.97 (1H, d, J=4 Hz), 7.19-7.36 (13H, m), 7.73 (2H, d, J=8 Hz), 9.72 (1H, br).

(4) Synthesis of Compound 5

In a stream of nitrogen, 20% palladium hydroxide-carbon powder (0.60 g) and cyclohexene (5.2 ml, 51 mmols) were added to an ethanol solution (10 ml) of Compound 4 (0.80 g, 1.28 mmols), and the mixture was refluxed with heating for 5 hours. Further, palladium hydroxide-carbon powder (0.20 g) was added, and the mixture was refluxed with heating for 17 hours. After the reaction solution was filtered, the solvent was distilled off under reduced pressure. The resulting crude product 5 (0.46 g) was used for a next reaction without being purified.

[Equation 4]

mp 103-106° C. $^1$H-NMR (CDCl$_3$) δ: 1.85 (3H, d, J=1 Hz), 2.41 (3H, s), 3.67 (2H, s), 4.14, 4.25 (2H, AB, J=11 Hz), 4.16 (1H, dd, J=4, 5 Hz), 4.21 (1H, d, J=4 Hz), 5.87 (1H, d, J=5 Hz), 7.38 (2H, d, J=8 Hz), 7.48 (1H, d, J=1 Hz), 7.79 (2H, d, J=8 Hz).

(5) Synthesis of Compound 6

In a stream of nitrogen, 1,3-dichloro-1,1,3,3-tetraisopropyldisiloxane (0.45 ml, 1.41 mmols) and imidazole (0.38 g, 5.63 mmols) were added to an N,N-dimethylformamide solution (10 ml) of Compound 5 (0.46 g), and the mixture was stirred for 5 hours at room temperature. The reaction mixture was extracted with ether, and the organic layer was washed with water and a saturated aqueous solution of sodium chloride, followed by drying the organic layer over magnesium sulfate. The solvent was distilled off under reduced pressure, and the resulting crude product was purified by silica gel column chromatography (n-hexane:ethyl acetate=2:1→1:1) to obtain Compound 6 (0.60 g, 68% from 4 in 2 steps) as a white solid.

[Equation 5]

mp 97-99° C. IR υ$_{max}$ (KBr): 3186, 3058, 2947, 2869, 1697, 1467, 1366, 1277, 1182, 1036, 1081, 1036 cm$^{-1}$. $^1$H-NMR (CDCl$_3$) δ: 0.82-1.29 (28H, m), 1.86 (3H, s), 2.45 (3H, s), 3.73, 4.01 (2H, AB, J=12 Hz), 4.06, 4.29 (2H, AB, J=11 Hz), 4.47 (1H, d, J=7 Hz), 4.52 (1H, dd, J=6, 7 Hz), 5.98 (1H, d, J=6 Hz), 7.28 (1H, s), 7.43 (2H, d, J=8 Hz), 7.81 (2H, d, J=8 Hz).

(6) Synthesis of Compound 7

In a stream of nitrogen, trifluoromethanesulfonic anhydride (0.15 ml, 0.88 mmol) and 4-(dimethylamino)pyridine (7 mg, 0.06 mmol) were added to a pyridine solution (3 ml) of Compound 6 (200 mg, 0.29 mmol) under ice-cooled conditions, and the mixture was stirred for 7.5 hours at room temperature. Water was added to the reaction solution, and the mixture was extracted with dichloromethane. The organic layer was washed with a saturated aqueous solution of sodium bicarbonate, and a saturated aqueous solution of sodium chloride. Then, the organic layer was dried over anhydrous sodium sulfate. The solvent was distilled off under reduced pressure, and the resulting crude product 7 (0.29 g) was used for a next reaction without being purified.

[Equation 6]

IR υ$_{max}$ (KBr): 3178, 3069, 2948, 2874, 1695, 1465, 1424, 1365, 1281, 1214, 1143, 1088, 1038 cm$^{-1}$. $^1$H-NMR (CDCl$_3$) δ: 0.81-1.26 (28H, m), 1.92 (3H, s), 2.46 (3H, s), 3.77, 4.16 (2H, AB, J=12 Hz), 4.15, 4.42 (2H, AB, J=10 Hz), 5.42 (1H, d, J=7 Hz), 5.45 (1H, d, J=7 Hz), 6.89 (1H, s), 7.37 (2H, d, J=8 Hz), 7.82 (2H, d, J=8 Hz), 7.92 (1H, s).

(7) Synthesis of Compound 8

In a stream of nitrogen, N-hydroxyphthalimide (67 mg, 0.41 mmol) and 1,8-diazabicyclo[5.4.0]-7-undecene (61 ml, 0.41 mmol) were added, at room temperature, to an acetonitrile solution (3 ml) of Crude Product 7 (0.29 g) obtained in the preceding reaction, and the mixture was stirred for 12 hours at room temperature. The reaction solution was extracted with dichloromethane, and the organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (chloroform) to obtain Compound 8 (0.15 g, 61% from 6 in 2 steps) as a yellow solid.

[Equation 7]

mp 109-111° C. $^1$H-NMR (CDCl$_3$) δ: 0.99-1.31 (28H, m), 1.87 (3H, s), 1.42 (3H, s), 3.88, 4.19 (2H, AB, J=13 Hz), 4.41, 4.91 (2H, AB, J=12 Hz), 4.77 (1H, d, J=6 Hz), 4.80 (1H, d, J=6 Hz), 6.00 (1H, s), 7.32-7.37 (3H, m), 7.74-7.90 (6H, m).

(8) Synthesis of Compound 9

Hydrazine hydrate (0.12 ml, 2.38 mmols) was added to an ethanol solution (35 ml) of Compound 8 (1.16 g, 1.40 mmols), and the mixture was stirred for 10 minutes at room temperature. After the solvent of the reaction solution was distilled off, the residue was filtered, and the filtrate was extracted with ethyl acetate. The organic layer was washed with water and a saturated aqueous solution of sodium chloride. Then, the organic layer was dried over anhydrous sodium sulfate. The solvent was distilled off under reduced pressure, and the resulting crude product 9 (0.93 g) was used for a next reaction without being purified.

[Equation 8]

mp 117-119° C. $^1$H-NMR (CDCl$_3$) δ: 0.87-1.09 (28H, m), 1.92 (3H, d, J=1 Hz), 2.45 (3H, s), 3.83, 3.91 (2H, AB, J=12 Hz), 4.22, 4.57 (2H, AB, J=16 Hz), 4.41 (1H, dd, J=1, 7 Hz), 4.80 (1H, d, J=7 Hz), 5.35 (1H, d, J=1 Hz), 5.81 (1H, br), 7.12 (1H, d, J=1 Hz), 7.33 (2H, d, J=8 Hz), 7.81 (2H, d, J=8 Hz), 8.75 (1H, s).

(9) Synthesis of Compound 10

In a stream of nitrogen, a saturated aqueous solution of sodium bicarbonate (4.0 ml, 4.2 mmols) and benzyl chloroformate (0.30 ml, 2.1 mmols) were added, under ice-cooled conditions, to a methylene chloride solution (15 ml) of Crude Product 9 (0.93 g) obtained in the preceding reaction, and the mixture was stirred for 1 hour. A saturated aqueous solution of sodium bicarbonate was added to the reaction solution, and the mixture was extracted with ethyl acetate. The organic layer was washed with water and a saturated aqueous solution of sodium chloride, followed by drying the organic layer over magnesium sulfate. The solvent was distilled off under reduced pressure, and the resulting crude product was purified by silica gel column chromatography (n-hexane:ethyl acetate=4:1) to obtain Compound 10 (0.92 g, 94% from 8 in 2 steps) as a white solid.

[Equation 9]

mp 82-84° C. IR υ$_{max}$ (KBr): 3319, 3059, 2948, 2874, 1691, 1464, 1365, 1245, 1180, 1098, 1034 cm$^{-1}$. $^1$H-NMR (CDCl$_3$) δ: 0.86 (28H, m), 1.87 (3H, a), 2.43 (3H, s), 3.80, 3.88 (2H, AB, J=11 Hz), 4.25, 4.53 (2H, AB, J=11 Hz), 4.72 (1H, d, J=6 Hz), 5.02 (1H, d, J=6 Hz), 5.15, 5.20 (2H, AB, J=12 Hz), 6.37 (1H, s), 7.31 (2H, d, J=8 Hz), 7.34 (5H, s), 7.80 (2H, d, J=8 Hz), 7.95 (1H, s), 8.48 (1H, s).

(10) Synthesis of Compound 11

In a stream of nitrogen, a tetrahydrofuran solution (15 ml) Compound 10 (3.81 g, 4.57 mmols) was added dropwise, under ice-cooled conditions, to a tetrahydrofuran suspension (25 ml) of sodium hydride (60% in oil, 0.55 g, 13.7 mmols), and the mixture was stirred for 1 hour, followed by stirring the mixture for 5 hours at room temperature. After neutralization in a saturated aqueous solution of oxalic acid, the reaction mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (chloroform→chloroform→methanol=100:1) to obtain Compound 11 (2.87 g, 95%) as a white solid.

[Equation 10]

mp 61-64° C. IR υ$_{max}$ (KBr): 3178, 3026, 2941, 2864, 1697, 1463, 1271, 1221, 1164, 1073 cm$^{-1}$. $^1$H-NMR (CDCl$_3$) δ: 0.80-1.12 (28H, m), 1.92 (3H, s), 3.62, 3.85 (2H, AB, J=12 Hz), 3.68, 4.11 (2H, AB, J=13 Hz), 4.11 (1H, d, J=4 Hz), 4.55 (1H, d, J=4 Hz), 6.21, 5.28 (2H, AB, J=12 Hz), 5.98 (1H, s), 7.30-7.44 (5H, m), 7.61 (1H, s), 8.80 (1H, br).

(11) Synthesis of Compound 12

In a stream of nitrogen, a 1M hexane solution of boron trichloride (5.29 ml, 5.29 mmols) was added, under ice-cooled conditions, to a methylene chloride solution (10 ml) of Crude Product 11 (0.35 mg, 0.53 mmol) obtained in the preceding reaction, and the mixture was stirred for 1 hour. A saturated aqueous solution of sodium bicarbonate was added to the reaction solution, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (chloroform:methanol=50:1) to obtain Compound 12 (0.27 g, 96%) as a white solid.

[Equation 11]

mp 102-104° C. IR υ$_{max}$ (KBr): 4326, 3178, 3059, 2947, 2864, 1698, 1564, 1464, 1270, 1043 cm$^{-1}$. $^1$H-NMR (CDCl$_3$) δ 0.99-1.25 (28H, m), 1.93 (3H, s), 2.54, 3.68 (2H, AB, J=13 Hz), 3.67, 4.06 (2H, AB, J=13 Hz), 4.10 (1H, d, J=2 Hz), 4.36 (1H, d, J=2 Hz), 6.17 (1H, s), 7.73 (1H, s), 8.71 (1H, br).

(12) Synthesis of Compound 13

A 20% aqueous solution of formaldehyde (0.06 ml, 0.40 mmol) was added to a 1M pyridinium p-toluenesulfonate-methanol solution (3.6 ml) of Compound 12 (0.19 g, 0.36 mmol) at room temperature, and the mixture was stirred for 10 minutes. Further, sodium cyanoborohydride (45 mg, 0.72 mmol) was added under ice-cooled conditions, and the mixture was stirred for 1 hour. The reaction solution was extracted with ethyl acetate, the extract was washed with water, a saturated aqueous solution of sodium bicarbonate, and a saturated aqueous solution of sodium chloride, and the organic layer was dried over anhydrous sodium sulfate. The solvent was distilled off under reduced pressure, and the resulting crude product was purified by silica gel column chromatography (n-hexane:ethyl acetate=2:1) to obtain Compound 13 (0.19 g, 100%) as a white solid.

[Equation 12]

IR υ$_{max}$ (KBr): 2947, 2868, 1695, 1464, 1267, 1163, 1038 cm$^{-1}$. $^1$H-NMR (CDCl$_3$) δ: 0.94-1.12 (28H, m), 1.92 (3H, d, J=1 Hz), 2.60, 2.91 (2H, AB, J=11 Hz), 2.76 (3H, s), 3.67, 4.08 (2H, AB, J=13 Hz), 3.95 (1H, d, J=3 Hz), 4.33 (1H, d, J=3 Hz), 6.24 (1H, s), 7.73 (1H, d, J=1 Hz), 8.56 (1H, br).

(13) Synthesis of Compound 14

Tetra-n-butylammonium fluoride (1M in tetrahydrofuran, 0.17 ml, 0.17 mmol) was added to a tetrahydrofuran solution (2 ml) of Compound 13 (46 mg, 0.085 mmol), and the mixture was stirred for 5 minutes at room temperature. The solvent was distilled off under reduced pressure, and the resulting crude product was purified by silica gel column chromatography (ethyl acetate:methanol=15:1) to obtain Compound 14 (25 mg, 100%) as a white solid.

[Equation 13]

mp 101-103° C. 1H-NMCR (CD$_3$OD) δ: 1.85 (3H, d, J=1 Hz), 2.71 (3H, s), 2.71, 2.88 (2H, AB, J=11 Hz), 3.69, 3.76 (2H, AB, J=12 Hz), 3.94 (1H, d, J=3 Hz), 4.23 (1H, d, J=3 Hz), 6.21 (1H, s), 7.99 (1H, d, J=1 Hz).

(14) Synthesis of Compound 15

To a pyridine solution (10 ml) of Compound 14 (0.16 g, 0.54 mmol), 4,4'-dimethoxytrityl chloride (0.22 g, 0.64 mmol) was added, and the mixture was stirred for 12 hours at room temperature. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (1% triethylamine-containing n-hexane:ethyl acetate=1:2→ethyl acetate:methanol=30:1) to obtain Compound 15 (0.30 g, 93%) as a white solid.

[Equation 14]

mp 133-134° C. $^1$H-NMR (CDCl$_3$) δ: 1.45 (3H, d, J=1 Hz), 2.62 (1H, d, J=9 Hz), 2.72 (3H, s), 2.77 (2H, s), 3.32, 3.37 (2H, AB, J=11 Hz), 3.79 (6H, s), 4.23 (1H, dd, J=3, 9 Hz), 4.35 (1H, d, J=3 Hz), 6.35 (1H, s), 6.84 (4H, d, J=8 Hz), 7.22-7.46 (9H, m), 7.75 (1H, d, J=1 Hz), 8.25 (1H, br).

(15) Synthesis of Compound 16

To an acetonitrile solution (6 ml) of Compound 15 (0.17 g, 0.28 mmol) and 4,5-dicyanoimidazole (40 mg, 0.34 mmol), 2-cyanoethyl-N,N,N',N'-tetraisopropylphosphoroamidite (0.13 ml, 0.42 mmol) was added, and the mixture was stirred for 4 hours at room temperature. A saturated aqueous solution of sodium bicarbonate was added to the reaction mixture, and the mixture was extracted with ethyl acetate. The organic layer was washed with a saturated aqueous solution of sodium bicarbonate, water, and a saturated aqueous solution of sodium chloride, followed by drying the organic layer over anhydrous sodium sulfate. The solvent was distilled off under reduced pressure, and the resulting crude product was purified by silica gel column chromatography (1% triethylamine-containing n-hexane:ethyl acetate=1:1), followed by reprecipitation (ethyl acetate-hexane) to obtain Compound 16 (0.20 g, 88%) as a white solid.

[Equation 15]

mp 65-65° C. $^{31}$P-NMR (acetone-d$_6$) δ: 148.69, 149.82.

(16) Synthesis of Compound 17

In a stream of nitrogen, phosphoryl chloride (86 ml, 0.92 mmol) was added, under ice-cooled conditions, to an acetonitrile suspension (9 ml) of 1,2,4-triazole (278 mg, 4.03 mmols), and the mixture was stirred vigorously for 10 minutes. Further, triethylamine (0.64 ml, 4.62 mmols) was added, and the mixture was stirred for 35 minutes. Under ice-cooled conditions, an acetonitrile solution (3 ml) of Compound 16 (95 mg, 0.12 mmol) was added, and the mixture was stirred for 5.5 hours. Then, the mixture was further stirred for 2.5 hours at room temperature. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (n-hexane:ethyl acetate=1:2), and then reprecipitation (ethyl acetate-hexane) to obtain Compound 17 (83 mg, 83%) as a white solid.

[Equation 16]

mp 107-109° C. $^{31}$P-NMR (acetone-d$_6$) δ: 148.24, 149.91.

(17) Synthesis of Compound 18

Phenoxyacetyl chloride (29 ml, 0.21 mmol) was added, under ice-cooled conditions, to a methylene chloride solution (3 ml) of Compound 12 (100 mg, 0.19 mmol) and triethylamine (32 ml, 0.12 mmol), and the mixture was stirred for 30 minutes. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (n-hexane:ethyl acetate=2:1) to obtain Compound 18 (115 mg, 92%) as a white solid.

[Equation 17]

mp 124-126° C. $^1$H-NMR (CDCl$_3$) δ: 1.02-1.13 (28H, m), 1.92 (3H, s), 3.49 (1H, AB, J=13 Hz), 3.73 (1H, AB, J=14 Hz), 4.16 (1H, d, J=3 Hz), 4.18 (1H, AB, J=13 Hz), 4.23 (1H, AB, J=14 Hz), 4.57 (1H, d, J=3 Hz), 4.91 (1H, AB, J=16 Hz), 5.00 (1H, AB, J=16 Hz), 5.97 (1H, s), 6.92-7.00 (3H, m), 7.24-7.30 (2H, m), 7.60 (1H, s), 9.69 (1H, brs).

(18) Synthesis of Compound 19

In a stream of nitrogen, tetra-n-butylammonium fluoride (1M tetrahydrofuran solution, 1.0 ml, 1.0 mmol) was added to a tetrahydrofuran solution (10 ml) of Compound 18 (0.34 g, 0.51 mmol) at room temperature, and the mixture was stirred for 5 minutes. The solvent was distilled off under reduced pressure, and the resulting crude product was purified by silica gel column chromatography (ethyl acetate:methanol=15:1) to obtain Compound 19 (0.20 g, 95%) as a white solid.

[Equation 18]

mp 144-146° C. $^1$H-NMR (CD$_3$OD) δ: 1.85 (3H, s), 3.53 (1H, AB, J=13 Hz), 3.77 (1H, AB, J=13 Hz), 3.85 (1H, AB, J=13 Hz), 4.18 (1H, AB, J=13 Hz), 4.20 (1H, d, J=2 Hz), 4.60 (1H, d, J=2 Hz), 4.93 (1H, AB, J=16 Hz), 5.04 (1H, AB, J=16 Hz), 6.05 (1H, s), 6.91-6.97 (3H, m), 7.23-7.28 (2H, m), 7.90 (1H, s).

(19) Synthesis of Compound 20

In a stream of nitrogen, 4,4'-dimethoxytrityl chloride (0.25 g, 0.73 mmol) was added to a pyridine solution (8 ml) of Compound 19 (0.17 g, 0.41 mmol) at room temperature, and the mixture was stirred for 7 hours. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (1% triethylamine-containing n-hexane:ethyl acetate=1:1→ethyl acetate:methanol=50:1) to obtain Compound 20 (0.25 g, 86%) as a white solid.

[Equation 19]

mp 144-145° C. $^1$H-NMR (CDCl$_3$) δ: 1.44 (3H, s), 2.65 (1H, br), 3.40 (1H, AB, J=11 Hz), 3.44 (1H, AB, J=13 Hz), 3.62 (1H, AB, J=11 Hz), 3.80 (6H, s), 4.23 (1H, AB, J=13 Hz), 4.44 (1H, d, J=3 Hz), 4.63 (1H, d, J=3 Hz), 4.86 (1H, AB, J=16 Hz), 4.99 (1H, AB, J=16 Hz), 6.04 (1H, s), 6.83-6.98 (7H, m), 7.25-7.43 (11H, m), 7.65 (1H, s), 8.38 (1H, br).

(20) Synthesis of Compound 21

To an acetonitrile solution (7 ml) of Compound 20 (0.25 g, 0.35 mmol) and 4,5-dicyanoimidazole (41 mg, 0.35 mmol), 2-cyanoethyl-N,N,N',N'-tetraisopropylphosphoroamidite (0.13 ml, 0.42 mmol) was added, and the mixture was stirred for 3 hours at room temperature. A saturated aqueous solution of sodium bicarbonate was added to the reaction mixture, and the mixture was extracted with ethyl acetate. The organic layer was washed with a saturated aqueous solution of sodium bicarbonate, water, and a saturated aqueous solution of sodium chloride, followed by drying the organic layer over anhydrous sodium sulfate. The solvent was distilled off under reduced pressure, and the resulting crude product was purified by silica gel column chromatography (1% triethylamine-containing n-hexane:ethyl acetate=1:1), followed by reprecipitation (ethyl acetate-hexane) to obtain Compound 21 (0.27 g, 85%) as a white solid.

[Equation 20]

mp 107-109° C. $^{31}$P-NMR (acetone-$d_6$) δ: 149.79, 151.04.

(21) Synthesis of Compound 22

In a stream of nitrogen, phosphoryl chloride (71 ml, 0.76 mmol) was added, under ice-cooled conditions, to an acetonitrile suspension (10 ml) of 1,2,4-triazole (229 mg, 3.32 mmols), and the mixture was stirred vigorously for 10 minutes. Further, triethylamine (0.53 ml, 3.81 mmols) was added, and the mixture was stirred for 35 minutes. Under ice-cooled conditions, an acetonitrile solution (2 ml) of Compound 21 (90 mg, 0.10 mmol) was added, and the mixture was stirred for 5 hours. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by reprecipitation (ethyl acetate-hexane) to obtain Compound 22 (90 mg, 95%) as a white solid.

[Equation 21]

mp 104-106° C. $^{31}$P-NMR (acetone-$d_6$) δ: 149.58, 151.29.

(22) Synthesis of Compound 23

In a stream of nitrogen, phosphoryl chloride (0.44 ml, 4.67 mmols) was added, under ice-cooled conditions, to an acetonitrile suspension (61 ml) of 1,2,4-triazole (1.41 g, 20.4 mmols), and the mixture was stirred vigorously for 10 minutes. Further, triethylamine (3.27 ml, 23.4 mmols) was added, and the mixture was stirred for 35 minutes. Under ice-cooled conditions, an acetonitrile solution (3 ml) of Compound 11 (409 mg, 0.62 mmol) was added, and the mixture was stirred for 2 hours, and further stirred for 3 hours at room temperature. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product 23 (497 mg) was used for a next reaction without being purified.

[Equation 22]

$^1$H-NMR (CDCl$_3$) δ: 0.92-1.12 (28H, m), 2.47 (3H, s), 3.66 (1H, AB, J=12 Hz), 3.72 (1H, AB, J=13 Hz), 3.90 (1H, AB, J=12 Hz), 4.06 (1H, d, J=3 Hz), 4.16 (1H, AB, J=13 Hz), 4.73 (1H, d, J=3 Hz), 6.11 (1H, s), 7.25-7.48 (5H, m), 8.12 (1H, s), 8.24 (1H, s), 9.32 (1H, s).

(23) Synthesis of Compound 24

To a 1,4-dioxane solution (10.6 ml) of Compound 23 (497 mg), a 28% aqueous solution of ammonia (1.76 ml) was added, and the mixture was stirred for 2 hours at room temperature. The solvent was distilled off under reduced pressure, and the resulting crude product was purified by silica gel column chromatography (chloroform:methanol=30:1) to obtain Compound 24 (343 mg, 84% from 11 in 2 steps) as a white solid.

[Equation 23]

mp 137-139° C. $^1$H-NMR (CDCl$_3$) δ: 0.93-1.11 (28H, m), 2.03 (3H, s), 3.62 (1H, AB, J=12 Hz), 3.69 (1H, AB, J=13 Hz), 3.85 (1H, AB, J=12 Hz), 4.03 (1H, d, J=3 Hz), 4.11 (1H, AB, J=13 Hz), 4.59 (1H, d, J=3 Hz), 5.24 (2H, s), 6.03 (1H, s), 7.26-7.45 (5H, m), 7.74 (1H, s).

(24) Synthesis of Compound 25

A saturated aqueous solution of sodium bicarbonate (0.8 ml, 0.79 mmol) and benzoyl chloride (92 ml, 0.79 mmol) were added to a methylene chloride solution (2.6 ml) of Compound 24 (175 mg, 0.26 mmol) under ice-cooled conditions, and the mixture was stirred for 2 hours, and further stirred for 1.5 hours at room temperature. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (chloroform) to obtain Compound 25 (161 mg, 80%) as a white solid.

[Equation 24]

mp 216-218° C. $^1$H-NMR (CDCl$_3$) δ: 0.99-1.12 (28H, m), 2.12 (3H, s), 3.63 (1H, AB, J=12 Hz), 3.70 (1H, AB, J=13 Hz), 3.87 (1H, AB, J=12 Hz), 4.11 (1H, d, J=3 Hz), 4.13 (1H, AB, J=13 Hz), 4.59 (1H, d, J=3 Hz), 5.22 (1H, AB, J=12 Hz), 5.29 (1H, AB, J=12 Hz), 6.02 (1H, s), 7.31-7.53 (8H, m), 7.88 (1H, s), 8.30-8.33 (2H, m).

(25) Synthesis of Compound 26

In a stream of nitrogen, a 1M hexane solution of boron trichloride (1.35 ml, 1.35 mmols) was added, while being cooled at −78° C., to a methylene chloride solution (7.5 ml) of Compound 25 (115 mg, 0.15 mmol), and the mixture was stirred for 1.5 hours, and further stirred for 2.5 hours under ice-cooled conditions. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product 26 (90 mg) was used for a next reaction without being purified.

[Equation 25]

$^1$H-NMR (CDCl$_3$) δ: 0.99-1.13 (28H, m), 2.14 (3H, s), 2.57 (1H, AB, J=13 Hz), 3.69 (1H, AB, J=14 Hz), 3.70 (1H, AB, J=13 Hz), 4.09 (1H, AB, J=14 Hz), 4.11 (1H, d, J=3 Hz), 4.42 (1H, d, J=3 Hz), 6.22 (1H, s), 7.42-7.56 (3H, m), 7.91 (1H, s), 8.30-8.33 (2H, m).

(26) Synthesis of Compound 27

In a stream of nitrogen, phenoxyacetyl chloride (23 ml, 0.17 mmol) was added, under ice-cooled conditions, to a methylene chloride solution (1.5 ml) of Compound 26 (90 mg) and triethylamine (25 ml, 0.18 mmol), and the mixture was stirred for 45 minutes. A saturated aqueous solution of sodium bicarbonate was added to the reaction mixture, and the mixture was extracted with ethyl acetate. The organic layer was washed with water and a saturated aqueous solution of sodium chloride, followed by drying the organic layer over anhydrous sodium sulfate. The solvent was distilled off under reduced pressure, and the resulting crude product was purified by silica gel column chromatography (n-hexane:ethyl acetate=2:1) to obtain Compound 27 (49 mg, 42% from 23 in 2 steps) as a white solid.

[Equation 26]

mp 224-226° C. $^1$H-NMR (CDCl$_3$) δ: 0.99-1.14 (28H, m), 2.13 (3H, s), 3.52 (1H, AB, J=13 Hz), 3.75 (1H, AB, J=13 Hz), 4.17 (1H, AB, J=13 Hz), 4.18 (1H, d, J=3 Hz), 4.23 (1H, AB, J=13 Hz), 4.61 (1H, d, J=3 Hz), 4.92 (1H, AB, J=16 Hz), 5.05 (1H, AB, J=16 Hz), 6.01 (1H, s), 6.95-7.02 (3H, m), 7.29 (2H, m), 7.42-7.57 (4H, m), 7.79 (1H, s), 8.30-8.33 (2H, m).

(27) Synthesis of Compound 28

In a stream of nitrogen, tetra-n-butylammonium fluoride (1M tetrahydrofuran solution, 0.12 ml, 0.12 mmol) was added, at room temperature, to a tetrahydrofuran solution (1.2 ml) of Compound 27 (45 mg, 0.06 mmol), and the mixture was stirred for 10 minutes. The solvent was distilled off under reduced pressure, and the resulting crude product was purified by silica gel column chromatography (n-hexane:ethyl acetate=1:1) to obtain Compound 28 (31 mg, 100%) as a white solid.

[Equation 27]

mp 148-150° C. $^1$H-NMR (pyridine-$d_5$) δ: 1.94 (3H, s), 4.08 (1H, AB, J=13 Hz), 4.23 (1H, AB, J=12 Hz), 4.30 (1H, AB, J=12 Hz), 4.73 (1H, AB, J=13 Hz), 5.21 (1H, AB, J=16 Hz), 6.28 (1H, d, J=3 Hz), 5.42 (1H, AB, J=16 Hz), 5.42 (1H, d, J=3 Hz), 6.61 (1H, s), 6.95-7.00 (1H, m), 7.27-7.36 (4H, m), 7.45-7.54 (3H, m), 7.73 (1H, s), 8.54-8.56 (2H, m).

Example 2

Synthesis and Purification of Oligonucleotide Analogues (1) Synthesis of 2',4'-BNA$^{NC}$ Modified Oligonucleotides Oligonucleotide analogues (1) to (22) containing 2',4'-BNA$^{NC}$ monomer units were synthesized by an automated nucleic acid synthesizer Expedite™ 8909 (ABI) on a 0.2 mmol scale in accordance with a standard phosphoroamidite protocol. The coupling time for the amidite and the 5'-terminal hydroxyl group was set at 94 seconds for the natural nucleoside amidite and at 300 seconds for the 2',4'-BNA$^{NC}$ amidites (16, 17 and 21).

For the 2',4'-BNA$^{NC}$ modified oligonucleotides having the 5'-terminal protected with a DMTr group and supported in a solid phase, removal (1.5 h) from a column using 28% aqueous ammonia was performed. The removed oligonucleotide analogues were reacted for 16 hours at 60° C. in 28% aqueous ammonia for deprotection of all protective groups.

Simple purification by an NAP-10 column was carried out, and respective fractions obtained were subjected to UV analysis.

Based on the results of the UV measurements, oligo-containing fractions were lyophilized, and the lyophilizates were further purified by reversed phase HPLC (WakoPak® WS-DNA column, 10.0 mm×250 mm) (conditions: gradient elution with 8-16% acetonitrile for 30 min at a rate of 3 ml/min in 0.1M triethylammonium acetate buffer (pH 7.0)). The purity of the synthetic oligonucleotide analogues was confirmed by reversed phase HPLC (WakoPak® WS-DNA column, 4.6 mm×250 mm) (conditions: gradient elution with 8-16% acetonitrile for 30 min at a rate of 1 ml/min in 0.1M triethylammonium acetate buffer (pH 7.0)). The molecular weights were determined by MALDI-TOF-MASS measurement.

The synthetic oligonucleotide analogues (1) to (22) are indicated below. (SEQ ID NOS: 1-22, respectively)

[Chemical formula 7]

| | |
|---|---|
| (1) | 5'-GCGTTXTTTGCT-3' |
| (2) | 5'-GCGTTXTXTGCT-3' |
| (3) | 5'-GCGXTXTXTGCT-3' |
| (4) | 5'-GCGTTXXXTGCT-3' |
| (5) | 5'-GCGXXXXXXGCT-3' |
| (6) | 5'-TTTTT$^m$CTXT$^m$CT$^m$CT-3' |
| (7) | 5'-TTTTTX$^m$CTXT$^m$CX$^m$CT-3' |

[Chemical formula 7]

| | |
|---|---|
| (8) | 5'-TTTTT$^m$CXXX$^m$CT$^m$CT$^m$CT-3' |
| (9) | 5'-XTXTX$^m$CXTX$^m$CX$^m$CX$^m$CT-3' |
| ⑩ | 5'-TXTTX$^m$CTXT$^m$CX$^m$CTX*T-3' |
| ⑪ | 5'-XTTTX$^m$CTTX$^m$CT$^m$CX$^m$CT-3' |
| ⑫ | 5'-TTTTTTTTXT-3' |
| ⑬ | 5'-GCGTTYTTTGCT-3' |
| ⑭ | 5'-GCGTTYTYTGCT-3' |
| ⑮ | 5'-GCGYTYTYTGCT-3' |
| ⑯ | 5'-GCGTTYYYTGCT-3' |
| ⑰ | 5'-GCGYYYYYYGCT-3' |
| ⑱ | 5'-TTTTT$^m$CTYT$^m$CT$^m$CT-3' |
| ⑲ | 5'-TTTTY$^m$CTYT$^m$CY$^m$CT-3' |
| ⑳ | 5'-TTTTT$^m$CYYY$^m$CT$^m$CT-3' |
| (21) | 5'-YTYTY$^m$CYYY$^m$CY$^m$CY$^m$CT-3' |
| (22) | 5'-TTTTTTTTYT-3' |

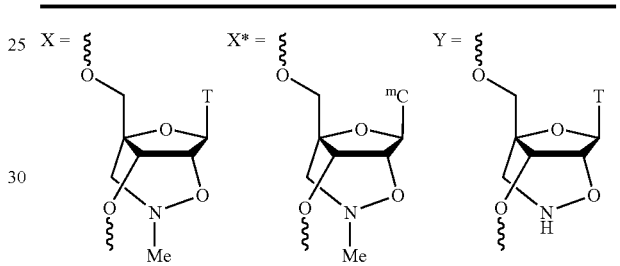

The amounts and yields of the 2',4'-BNA$^{NC}$ modified oligonucleotides obtained are shown below. (SEQ ID NOS: 1-12, respectively)

TABLE 1

| Oligonucleotide | Amount obtained (nmol) | Yield (%) |
|---|---|---|
| ① 5'-GCGTTXTTTGCT-3' | 94.91 | 47.5 |
| ② 5'-GCGTTXTXTGCT-3' | 118.67 | 59.3 |
| ③ 5'-GCGXTXTXTGCT-3' | 126.12 | 63.1 |
| ④ 5'-GCGTTXXXTGCT-3' | 66.94 | 33.5 |
| ⑤ 5'-GCGXXXXXXGCT-3' | 99.40 | 49.7 |
| ⑥ 5'-TTTTT$^m$CTXT$^m$CT$^m$CT-3' | 72.44 | 36.2 |
| ⑦ 5'-TTTTX$^m$CTXT$^m$CX$^m$CT-3' | 61.07 | 30.6 |
| ⑧ 5'-TTTTT$^m$CXXX$^m$CT$^m$CT-3' | 60.40 | 30.2 |
| ⑨ 5'-XTXTX$^m$CXTX$^m$CX$^m$CT-3' | 41.60 | 20.8 |
| ⑩ 5'-TXTTX$^m$CTXT$^m$CX$^m$CTX*T-3' | 25.40 | 12.7 |
| ⑪ 5'-XTTTX$^m$CTTX$^m$CT$^m$CX$^m$CT-3' | 81.80 | 40.9 |
| ⑫ 5'-TTTTTTTTXT-3' | 100.13 | 50.1 |

Furthermore, the results of the MALDI-TOF MS measurement of the synthetic 2',4'-BNA$^{NC}$ modified oligonucleotides are tabulated below. (SEQ ID NOS: 1-22, respectively)

TABLE 2

| Oligonucleotides | | Calcd. For (M-H) | Found (M-H) |
|---|---|---|---|
| ① | 5'-GCGTTXTTTGCT-3' | 3689.47 | 3688.52 |
| ② | 5'-GCGTTXTXTGCT-3' | 3746.52 | 3746.89 |
| ③ | 5'-GCGXTXTXTGCT-3' | 3803.57 | 3804.93 |
| ④ | 5'-GCGTTXXXTGCT-3' | 3803.57 | 3803.18 |
| ⑤ | 5'-GCGXXXXXXGCT-3' | 3974.73 | 3975.31 |
| ⑥ | 5'-TTTTT$^m$CTXT$^m$CT$^m$CT$^m$CT-3' | 4553.11 | 4552.67 |
| ⑦ | 5'-TTTTX$^m$CTXT$^m$CX$^m$CT$^m$CT-3' | 4667.21 | 4667.36 |
| ⑧ | 5'-TTTTT$^m$CXXX$^m$CT$^m$CT$^m$CT-3' | 4667.21 | 4666.86 |
| ⑨ | 5'-XTXTX$^m$CXTX$^m$CX$^m$CX$^m$CT-3' | 4895.42 | 4896.42 |
| ⑩ | 5'-TXTTX$^m$CTXT$^m$CX$^m$CTX\*T-3' | 4781.32 | 4781.18 |
| ⑪ | 5'-XTTTX$^m$CTTX$^m$CT$^m$CX$^m$CT-3' | 4724.26 | 4723.73 |
| ⑫ | 5'-TTTTTTTTXT-3' | 3036.06 | 3036.36 |
| ⑬ | 5'-GCGTTYTTTGCT-3' | 3675.44 | 3675.80 |
| ⑭ | 5'-GCGTTYTYTGCT-3' | 3718.47 | 3717.15 |
| ⑮ | 5'-GCGYTYTYTGCT-3' | 3761.49 | 3762.64 |
| ⑯ | 5'-GCGTTYYYTGCT-3' | 3761.49 | 3761.24 |
| ⑰ | 5'-GCGYYYYYYGCT-3' | 3890.57 | 3890.62 |
| ⑱ | 5'-TTTTT$^m$CTYT$^m$CT$^m$CT$^m$CT-3' | 4539.08 | 4540.11 |
| ⑲ | 5'-TTTTY$^m$CTYT$^m$CY$^m$CT$^m$CT-3' | 4625.13 | 4625.74 |
| ⑳ | 5'-TTTTT$^m$CYYY$^m$CT$^m$CT$^m$CT-3' | 4625.13 | 4625.71 |
| (21) | 5'-YTYTY$^m$CYYY$^m$CY$^m$CY$^m$CT-3' | 4797.23 | 4797.80 |
| (22) | 5'-TTTTTTTTYT-3' | 3022.03 | 3021.9 |

Experimental Example 1

Measurement of Melting Points (Tm) of 2',4'-BNA$^{NC}$ Modified Oligonucleotides (Evaluation of Duplex-Forming Capacity)

The oligonucleotide analogues (1) to (5) and (13) to (17) synthesized in the Examples (i.e., antisense strands), and a sense strand of a natural DNA or RNA oligonucleotide were annealed. The melting points (Tm) of the annealing products were measured to investigate the duplex-forming capacity of the antisense strands.

Sample solutions (500 μL) with end concentrations of NaCl 100 mM, sodium phosphate buffer (pH 7.2) 10 mM, antisense strand 4 μM, and sense strand 4 μM were bathed in boiling water, and cooled down to room temperature over the course of 10 hours. A stream of nitrogen was flowed through a cell chamber of a spectrophotometer (Beckman, DU-650) to prevent dew formation, and the sample solutions were gradually cooled down to 5° C. Further, the sample solutions were maintained at 10° C. for 20 minutes, and then their measurements were started. The temperature was raised up to 90° C. at a rate of 0.5° C./min, and the ultraviolet absorption at 260 nm was measured.

The results are shown in Tables 3 (SEQ ID NOS: 23, 24. 1-5, 13-17, respectively) and 4 (SEQ ID NOS: 25. 24, 1-5, 13-17, respectively).

TABLE 3

Duplex-forming capacity with DNA strand (5'-AGCAAAAAACGC-3') (Tm value evaluation): ° C.

| Antisense strand | | Tm | ΔTm/mod. |
|---|---|---|---|
| | 5'-GCGTTTTTTGCT-3' | 50 | Natural |
| ① | 5'-GCGTTXTTTGCT-3' | 49 | -1 |
| ② | 5'-GCGTTXTXTGCT-3' | 49 | -0.5 |
| ③ | 5'-GCGXTXTXTGCT-3' | 51 | -0.3 |
| ④ | 5'-GCGTTXXXTGCT-3' | 50 | 0 |
| ⑤ | 5'-GCGXXXXXXGCT-3' | 61 | +1.8 |
| ⑬ | 5'-GCGTTYTTTGCT-3' | 51 | +1 |
| ⑭ | 5'-GCGTTYTYTGCT-3' | 52 | +1 |
| ⑮ | 5'-GCGYTYTYTGCT-3' | 55 | +1.7 |
| ⑯ | 5'-GCGTTYYYTGCT-3' | 57 | +2.3 |
| ⑰ | 5'-GCGYYYYYYGCT-3' | 73 | +3.8 |

Conditions: 100 mM NaCl, 10 mM Na2HPO4 buffer (pH7.2), [strand] = 4 μM. Tm was the average value of 3 or more experiments.

TABLE 4

Duplex-forming capacity with RNA strand (5'-AGCAAAAAACGC-3') (Tm value evaluation): ° C.

| Antisense strand | | Tm | ΔTm/mod. |
|---|---|---|---|
| | 5'-GCGTTTTTTGCT-3' | 45 | Natural |
| ① | 5'-GCGTTXTTTGCT-3' | 50 | +5 |
| ② | 5'-GCGTTXTXTGCT-3' | 56 | +5.5 |
| ③ | 5'-GCGXTXTXTGCT-3' | 63 | +6 |
| ④ | 5'-GCGTTXXXTGCT-3' | 59 | +4.7 |
| ⑤ | 5'-GCGXXXXXXGCT-3' | 80 | +5.8 |
| ⑬ | 5'-GCGTTYTTTGCT-3' | 51 | +6 |
| ⑭ | 5'-GCGTTYTYTGCT-3' | 56 | +5.5 |
| ⑰ | 5'-GCGYTYTYTGCT-3' | 64 | +6.3 |
| ⑮ | 5'-GCGTTYYYTGCT-3' | 61 | +5.3 |
| ⑯ | 5'-GCGYYYYYYGCT-3' | 83 | +6.3 |

Conditions: 100 mM NaCl, 10 mM Na2HPO4 buffer (pH7.2), [strand] = 4 μM. Tm was the average value of 3 or more experiments.

Based on the above findings, the nucleotide analogues of the present invention have a much higher duplex-forming capacity with single-stranded RNA (sense strand) than their duplex-forming capacity with single-stranded DNA (sense strand), and are considered to be suitable for the antisense method.

Experimental Example 2

Measurement of Tm of 2',4'-BNA$^{NC}$ Modified Oligonucleotides (Evaluation of Triplex-Forming Capacity)

In connection with the oligonucleotide analogues (6) to (11) and (18) to (21) synthesized in the Examples, the triplex-forming capacity with the target double-stranded DNA's indicated below was investigated by the same method as in Experimental Example 1. The salt concentrations and pH during measurement complied with the conditions described below the respective tables.

The results and experimental conditions are shown in Table 5. Table 5-1 contains SEQ ID NOS: 26-28, 6-11, and 18-21, respectively. Table 5-2 contains SEQ ID NOS: 29,30,28, 6-11, and 18-21, respectively. Table 5-3 contains SEQ ID NOS: 31-33, 6, and 18. respectively.

TABLE 5-1

$T_m$ values of 2',4'-BNA$^{NC}$ oligonucleotides with dsDNA.
target: 5'-d(GCTAAAAAGAAAGAGAGATCG)-3'
3'-d(CGATTTTTCTTTCTCTCTAGC)-5'

| oligonucleotides | $T_m$ ($\Delta T_m$/modification) (° C.) |
|---|---|
| 5'-TTTTT$^m$CTTT$^m$CT$^m$CT$^m$CT-3' | 33 |
| (6) 5'-TTTTT$^m$CTXT$^m$CT$^m$CT$^m$CT-3' | 38 (+5.0) |
| (7) 5'-TTTTX$^m$CTXT$^m$CX$^m$CT$^m$CT-3' | 47 (+4.6) |
| (8) 5'-TTTTT$^m$CXXX$^m$CT$^m$CT$^m$CT-3' | 42 (+3.0) |

TABLE 5-1-continued $T_m$ values of 2',4'-BNA$^{NC}$ oligonucleotides with dsDNA.
target: 5'-d(GCTAAAAAGAAAGAGAGATCG)-3'
3'-d(CGATTTTTCTTTCTCTCTAGC)-5'

| oligonucleotides | $T_m$ ($\Delta T_m$/modification) (° C.) |
|---|---|
| (9) 5'-XTXTX$^m$CXTX$^m$CX$^m$CX$^m$CT-3' | 59 (+3.7) |
| (10)5'-TCTTC$^m$CTXp1 T$^m$CX$^m$CTX*T-3' | 50 (+3.4) |
| (11)5'-XTTTX$^m$CTTX$^m$CT$^m$CX$^m$CT-3' | 45 (+3.0) |
| (18)5'-TTTTT$^m$CTYT$^m$CT$^m$CT$^m$CT-3' | 44 (+11.0) |
| (19)5'-TTTTY$^m$CTYT$^m$CY$^m$CT$^m$CT-3' | 60 (+9.0) |
| (20)5'-TTTTT$^m$CYYY$^m$CT$^m$CT$^m$CT-3' | 59 (+8.7) |
| (21) 5'-YTYTY$^m$CYTY$^m$CY$^m$CY$^m$CT-3' | 78 (+6.4) |

Conditions: 140 mM KCl, 7 mM Na$_2$HPO$_4$ buffer (pH 7.0), each strand 1.5 µM, 5° C. to 90° C. (0.5° C./min).
X*:2',4'-BNA$^{NC}$(N-Me)-$^m$C

TABLE 5-2

$T_m$ values of 2',4'-BNA$^{NC}$ oligonucleotides with dsDNA.
target: 5'-d(GCTGCTAAAAAGAAAGAGAGATCGTCG)-3'
3'-d(CGACGATTTTTCTTTCTCTCTAGCAGC)-5'

| oligonucleotides | $T_m$ ($\Delta T_m$/modification) (° C.) |
|---|---|
| 5'-TTTTT$^m$CTTT$^m$CT$^m$CT$^m$CT-3' | 43 |
| (6) 5'-TTTTT$^m$CTXT$^m$CT$^m$CT$^m$CT-3' | 49 (+6.0) |
| (7) 5'-TTTTX$^m$CTXT$^m$CX$^m$CT$^m$CT-3' | 61 (+6.0) |
| (8) 5'-TTTTT$^m$CXXX$^m$CT$^m$CT$^m$CT-3' | 54 (+3.6) |
| (9) 5'-XTXTX$^m$CXTX$^m$CX$^m$CX$^m$CT-3' | >80 (>+5) |
| (10)5'-TXTTX$^m$CTXT$^m$CX$^m$CTX*T-3' | 63 (+4.0) |
| (11)5'-XTTTX$^m$CTTX$^m$CT$^m$CX$^m$CT-3' | 59 (+4.0) |
| (18)5'-TTTTT$^m$CTYT$^m$CT$^m$CT$^m$CT-3' | 55 (+12.0) |
| (20)5'-TTTTY$^m$CTYT$^m$CY$^m$CT$^m$CT-3' | 73 (+10.0) |
| (19)5'-TTTTT$^m$CYYY$^m$CT$^m$CT$^m$CT-3' | 71 (+9.3) |
| (21) 5'-YTYTY$^m$CYTY$^m$CY$^m$CY$^m$CT-3' | >80 (>+5) |

Conditions: 140 mM KCl, 10 mM MgCl$_2$, 7 mM Na$_2$HPO$_4$ buffer (pH 7.0), each strand 1.5 µM, 5° C. to 90° C. (0.5° C./min).
X*: 2',4'-BNA$^{NC}$(N-Me)-$^m$C

TABLE 5-3

Sequence selective triplex-formation of 2', 4'-BNA$^{NC}$ oligonucleotides.

target: 5'-d(TTTTT$^m$CTZT$^m$CT$^m$CT$^m$CT)-3'
5'-d(GCTAAAAAGAMAGAGAGATCG)-3'
3'-d(CGATTTTTCTNTCTCTCTAGC)-5'

| | | $T_m$ ($\Delta T_m$ = $T_{m(mismatch)}$ − $T_{m(match)}$) (° C.) | | | |
|---|---|---|---|---|---|
| Z | M · N = | A · T | G · C | C · G | T · A |
| natural-T | | 43 | 21 (−22) | 25 (−18) | 18 (−25) |
| (6) X[2',4'-BNA$^{NC}$(N-Me)] | | 50 | 24 (−26) | 22 (−28) | 14 (−36) |
| (18) Y[2',4'-BNA$^{NC}$(N-H)] | | 55 | 30 (−25) | 28 (−27) | 25 (−30) |

Conditions: 140 mM KCl, 7 mM sodium phosphate buffer (pH 7.0), each strand 1.5 µM, 5° C. to 90° C. (0.5° C./min), C: 2'-deoxy-5-methylcytidine.

As shown in Table 5, the oligonucleotide analogues (6) to (11) and (18) to (21) of the present invention were found to have an excellent triplex-forming capacity. Their sequence selectivity was also superior to that of the natural antisense strand. Thus, they are believed to be very useful for the antigene method as well.

Experimental Example 3

Measurement of Enzyme Resistance

Natural (DNA oligonucleotide) and nonnatural oligonucleotides shown below were examined for resistance to exonuclease which degrades the oligonucleotide from the 3'-side.

1) Each oligonucleotide and snake venom phosphodiesterase (Boehringer Mannheim) as 3'-exonuclease were added, at concentrations of 25 mg/mL and 0.5 mg/mL, into 400 mL of 50 mM Tris-HCl buffer (pH 8.0) containing 10 mM $MgCl_2$, and the mixture was held at 37° C.

2) After a constant period of time, the survival rate of each oligonucleotide was measured by HPLC.

The sequences of the oligonucleotides used in the measurement are shown below.

5'-TTTTTTTTXT-3' (SEQ ID NO: 34)

[Chemical Formula 8]

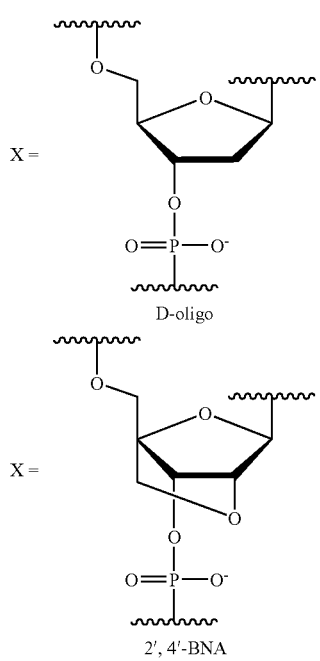

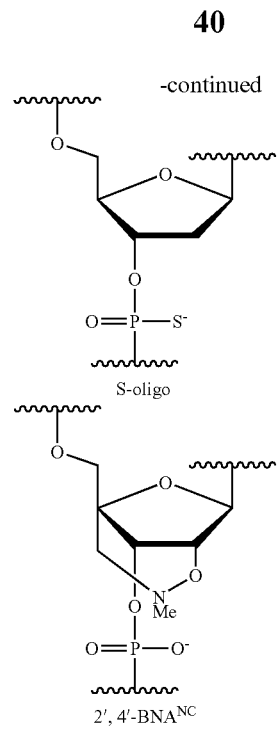

where when X is a DNA monomer, the oligonucleotide is a completely natural DNA oligonucleotide, and the oligonucleotide containing other nucleotide analogue is a partially non-natural oligonucleotide; moreover, the oligonucleotide analogue with X being 2',4'-$BNA^{NC}$(N-Me) is the oligonucleotide analogue of the present invention.

Changes over time in the survival rates of the respective oligonucleotides, measured by HPLC, are shown in Table 6 and FIG. 1.

In Table 6 and FIG. 1, "% of intact oligonucleotide" refers to the survival rate (%) (HPLC determination) of the undegraded oligonucleotide at measurement time points to the undegraded oligonucleotide at 0 time point.

TABLE 6

| | Evaluation of enzyme resistance | | | | | |
|---|---|---|---|---|---|---|
| | % of intact oligonucleotide | | | | | |
| oligonucleotide | 0 min | 5 min | 10 min | 20 min | 40 min | 90 min |
| D-oligo | 100 | 0 | 0 | 0 | 0 | 0 |
| 2',4'-BNA | 100 | 37 | 24 | 5 | 1 | 0 |
| S-oligo | 100 | 94 | 92 | 91 | 83 | 70 |
| 2',4'-$BNA^{NC}$ | 100 | 100 | 99 | 98 | 94 | 80 |

The results of Table 6 and FIG. 1 show that the oligonucleotide analogue of the present invention had excellent enzyme resistance as compared with natural and other nonnatural oligonucleotides.

The invention claimed is:
1. A compound of the following general formula (I) and a salt thereof:

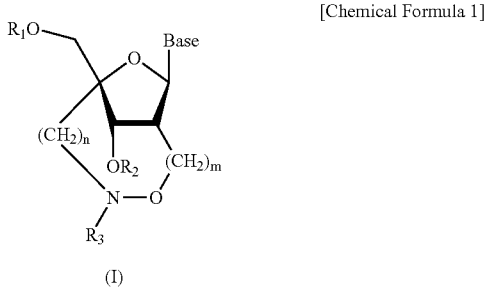

[Chemical Formula 1]

(I)

where Base represents an aromatic heterocyclic group or aromatic hydrocarbon ring group optionally having a substituent, $R_1$ and $R_2$ are identical or different, and each represent a hydrogen atom, a protective group for a hydroxyl group for nucleic acid synthesis, an alkyl group, an alkenyl group, a cycloalkyl group, an aryl group, an aralkyl group, an acyl group, a sulfonyl group, a silyl group, a phosphate group, a phosphate group protected with a protective group for nucleic acid synthesis, or —P($R_4$) $R_5$ where $R_4$ and $R_5$ are identical or different, and each represent a hydroxyl group, a hydroxyl group protected with a protective group for nucleic acid synthesis, a mercapto group, a mercapto group protected with a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted by an alky group having 1 to 5 carbon atoms, $R_3$ represents a hydrogen atom, an alkyl group, an alkenyl group, a cycloalkyl group, an aryl group, an aralkyl group, an acyl group, a sulfonyl group, or a functional molecule unit substituent, and m denotes an integer of 0 to 2, and n denotes an integer of 1 to 3.

2. The compound and the salts thereof according to claim 1, wherein $R_1$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, or a silyl group.

3. The compound and the salt thereof according to claim 1, wherein $R_1$ is a hydrogen atom, an acetyl group, a benzoyl group, a methanesulfonyl group, a p-toluenesulfonyl group, a benzyl group, a p-methoxybenzyl group, a trityl group, a dimethoxytrityl group, a monomethoxytrityl group, or a tert-butyldiphenylsilyl group.

4. The compound and the salts thereof according to any one of claims 1 to 3, wherein $R_2$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, a silyl group, a phosphoroamidite group, a phosphonyl group, a phosphate group, or a phosphate group protected with a protective group for nucleic acid synthesis.

5. The compound and the salt thereof according to any one of claims 1 to 3, wherein $R_2$ is a hydrogen atom, an acetyl group, a benzoyl group, a methanesulfonyl group, a p-toluenesulfonyl group, a benzyl group, a p-methoxybenzyl group, a tert-butyldiphenylsilyl group, —P($OC_2H_4CN$)(N(i-Pr)$_2$), —P($OCH_3$)(N(i-Pr)$_2$), a phosphonyl group, or a 2-chlorophenyl- or 4-chlorophenylphosphate group.

6. The compound and the salt thereof according to claim 1, wherein $R_3$ is a hydrogen atom, a phenoxyacetyl group, an alkyl group having 1 to 5 carbon atoms, an alkenyl group having 1 to 5 carbon atoms, an aryl group having 6 to 14 carbon atoms, a methyl group substituted by one to three aryl groups, a lower aliphatic or aromatic sulfonyl group such as a methanesulfonyl group or a p-toluenesulfonyl group, an aliphatic acyl group having 1 to 5 carbon atoms such as an acetyl group, or an aromatic acyl group such as a benzoyl group.

7. The compound and the salt thereof according to claim 1, wherein the functional molecule unit substituent as $R_3$ is a fluorescent or chemiluminescent labeling molecule, a nucleic acid incision activity functional group, or an intracellular or nuclear transfer signal peptide.

8. The compound and the salt thereof according to claim 1, wherein Base is a purin-9-yl group, a 2-oxopyrimidin-1-yl group, or a purin-9-yl group or a 2-oxopyrimidin-1-yl group having a substituent selected from the following α group:

α group: A hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom.

9. The compound and the salt thereof according to claim 1, wherein Base is 6-aminopurin-9-yl (i.e., adeninyl), 6-aminopurin-9-yl having the amino group protected with a protective group for nucleic acid synthesis, 2,6-diaminopurin-9-yl, 2-amino-6-chloropurin-9-yl, 2-amino-6-chloropurin-9-yl having the amino group protected with a protective group for nucleic acid synthesis, 2-amino-6-fluoropurin-9-yl, 2-amino-6-fluoropurin-9-yl having the amino group protected with a protective group for nucleic acid synthesis, 2-amino-6-bromopurin-9-yl, 2-amino-6-bromopurin-9-yl having the amino group protected with a protective group for nucleic acid synthesis, 2-amino-6-hydroxypurin-9-yl (i.e., guaninyl), 2-amino-6-hydroxypurin-9-yl having the amino group protected with a protective group for nucleic acid synthesis, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, 2-oxo-4-amino-1,2-dihydropyrimidin-1-yl (i.e., cytosinyl), 2-oxo-4-amino-1,2-dihydropyrimidin-1-yl having the amino group protected with a protective group for nucleic acid synthesis, 2-oxo-4-amino-5-fluoro-1,2-dihydropyrimidin-1-yl, 2-oxo-4-amino-5-fluoro-1,2-dihydropyrimidin-1-yl having the amino group protected with a protective group for nucleic acid synthesis, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydropyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), or 4-amino-5-methyl-2-oxo-1,2-dihydropyrimidin-1-yl having the amino group protected with a protective group for nucleic acid synthesis.

10. The compound and the salt thereof according to claim 1, wherein m is 0, and n is 1.

11. An oligonucleotide analogue, as a DNA oligonucleotide or RNA oligonucleotide analogue, containing one or two or more of one or more types of unit structures of nucleoside analogues represented by the following general formula (II), or a pharmacologically acceptable salt thereof, provided that a form of linking between respective nucleosides in the oligonucleotide analogue may contain one or two or more phosphorothioate bonds [—OP(O)(S⁻)O—] aside from a phosphodiester bond [—OP(O₂⁻)O—] identical with that in a natural nucleic acid, and if two or more of one or more types of these structures are contained, Base may be identical or different between these structures.

[Chemical Formula 2]

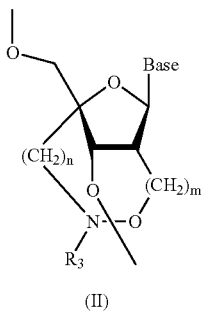

(II)

where Base represents an aromatic heterocyclic group or aromatic hydrocarbon ring group optionally having a substituent, $R_3$ represents a hydrogen atom, an alkyl group, an alkenyl group, a cycloalkyl group, an aryl group, an aralkyl group, an acyl group, a sulfonyl group, a silyl group, or a functional molecule unit substituent, and m denotes an integer of 0 to 2, and n denotes an integer of 1 to 3.

12. The oligonucleotide analogue or the pharmacologically acceptable salt thereof according to claim 11, wherein $R_1$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, or a silyl group.

13. The oligonucleotide analogue or the pharmacologically acceptable salt thereof according to claim 11, wherein $R_1$ is a hydrogen atom, an acetyl group, a benzoyl group, a methanesulfonyl group, a p-toluenesulfonyl group, a benzyl group, a p-methoxybenzyl group, a trityl group, a dimethoxytrityl group, a monomethoxytrityl group, or a tert-butyldiphenylsilyl group.

14. The oligonucleotide analogue or the pharmacologically acceptable salt thereof according to any one of claims 11 to 13, wherein $R_2$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, a silyl group, a phosphoroamidite group, a phosphonyl group, a phosphate group, or a phosphate group protected with a protective group for nucleic acid synthesis.

15. The oligonucleotide analogue or the pharmacologically acceptable salt thereof according to any one of claims 11 to 13, wherein $R_2$ is a hydrogen atom, an acetyl group, a benzoyl group, a benzyl group, a p-methoxybenzyl group, a methanesulfonyl group, a p-toluenesulfonyl group, a tert-butyldiphenylsilyl group, —P(OC₂H₄CN)(N(i-Pr)₂), —P(OCH₃)(N(i-Pr)₂), a phosphonyl group, or a 2-chlorophenyl- or 4-chlorophenylphosphate group.

16. The oligonucleotide analogue or the pharmacologically acceptable salt thereof according to claim 11, wherein $R_3$ is a hydrogen atom, a phenoxyacetyl group, an alkyl group having 1 to 5 carbon atoms, an alkenyl group having 1 to 5 carbon atoms, an aryl group having 6 to 14 carbon atoms, a methyl group substituted by one to three aryl groups, a lower aliphatic or aromatic sulfonyl group such as a methanesulfonyl group or a p-toluenesulfonyl group, an aliphatic acyl group having 1 to 5 carbon atoms such as an acetyl group, or an aromatic acyl group such as a benzoyl group.

17. The oligonucleotide analogue or the pharmacologically acceptable salt thereof according to claim 11, wherein the functional molecule unit substituent as $R_3$ is a fluorescent or chemiluminescent labeling molecule, a nucleic acid incision activity functional group, or an intracellular or nuclear transfer signal peptide.

18. The oligonucleotide analogue or the pharmacologically acceptable salt thereof according to claim 11, wherein Base is a purin-9-yl group, a 2-oxopyrimidin-1-yl group, or a purin-9-yl group or a 2-oxopyrimidin-1-yl group having a substituent selected from the following α group:

α group: A hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom.

19. The oligonucleotide analogue or the pharmacologically acceptable salt thereof according to claim 11, wherein Base is 6-aminopurin-9-yl (i.e. adeninyl), 6-aminopurin-9-yl having the amino group protected with a protective group for nucleic acid synthesis, 2,6-diaminopurin-9-yl, 2-amino-6-chloropurin-9-yl, 2-amino-6-chloropurin-9-yl having the amino group protected with a protective group for nucleic acid synthesis, 2-amino-6-fluoropurin-9-yl, 2-amino-6-fluoropurin-9-yl having the amino group protected with a protective group for nucleic acid synthesis, 2-amino-6-bromopurin-9-yl, 2-amino-6-bromopurin-9-yl having the amino group protected with a protective group for nucleic acid synthesis, 2-amino-6-hydroxypurin-9-yl (i.e., guaninyl), 2-amino-6-hydroxypurin-9-yl having the amino group protected with a protective group for nucleic acid synthesis, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, 2-oxo-4-amino-1,2-dihydropyrimidin-1-yl (i.e., cytosinyl), 2-oxo-4-amino-1,2-dihydropyrimidin-1-yl having the amino group protected with a protective group for nucleic acid synthesis, 2-oxo-4-amino-5-fluoro-1,2-dihydropyrimidin-1-yl, 2-oxo-4-amino-5-fluoro-1,2-dihydropyrimidin-1-yl group having the amino group protected with a protective group for nucleic acid synthesis, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydropyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), or 4-amino-5-methyl-2-oxo -1,2-dihydropyrimidin-1-yl having the amino group protected with a protective group for nucleic acid synthesis.

20. The oligonucleotide analogue or the pharmacologically acceptable salt thereof according to claim 11, wherein m is 0, and n is 1.

* * * * *

UNITED STATES PATENT AND TRADEMARK OFFICE
CERTIFICATE OF CORRECTION

PATENT NO. : 7,427,672 B2
APPLICATION NO. : 10/569949
DATED : September 23, 2008
INVENTOR(S) : Takeshi Imanishi et al.

It is certified that error appears in the above-identified patent and that said Letters Patent is hereby corrected as shown below:

Correct the structural formula at column 39, lines 32-43 to read

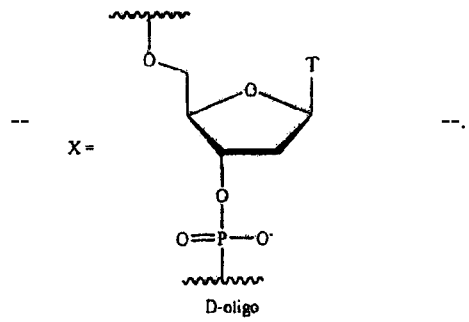

Correct the structural formula at column 39, lines 44-56 to read

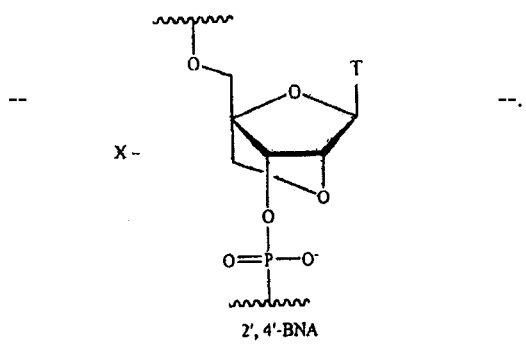

Signed and Sealed this

Twelfth Day of October, 2010

David J. Kappos
*Director of the United States Patent and Trademark Office*

CERTIFICATE OF CORRECTION (continued)
U.S. Pat. No. 7,427,672 B2

Correct the structural formula at column 40, lines 1-13 to read

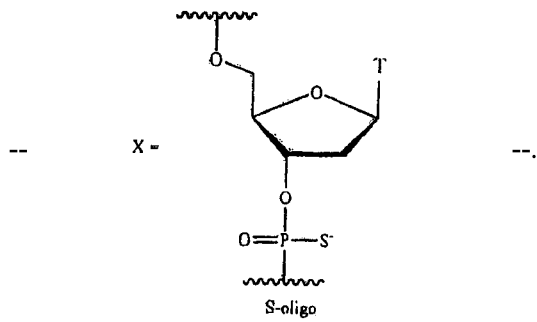

-- X - --.

Correct the structural formula at column 40, lines 14-26 to read

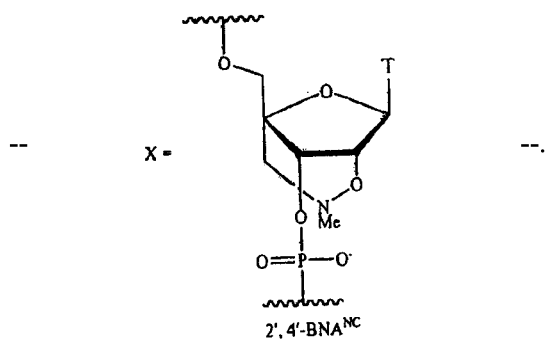

-- X - --.